(12) United States Patent
Matsui et al.

(10) Patent No.: US 12,324,730 B2
(45) Date of Patent: Jun. 10, 2025

(54) DISPOSABLE DIAPER

(71) Applicant: UNICHARM CORPORATION, Ehime (JP)

(72) Inventors: Takashi Matsui, Kanonji (JP); Yasuhiro Yamanaka, Kanonji (JP); Satoru Sakaguchi, Kanonji (JP)

(73) Assignee: Unicharm Corporation, Ehime (JP)

( * ) Notice: Subject to any disclaimer, the term of this patent is extended or adjusted under 35 U.S.C. 154(b) by 833 days.

(21) Appl. No.: 17/335,525

(22) Filed: Jun. 1, 2021

(65) Prior Publication Data

US 2021/0282981 A1 Sep. 16, 2021

Related U.S. Application Data

(63) Continuation of application No. PCT/JP2019/047736, filed on Dec. 6, 2019.

(30) Foreign Application Priority Data

Dec. 7, 2018 (JP) .................................. 2018-230409

(51) Int. Cl.
*A61F 13/475* (2006.01)
*A61F 13/49* (2006.01)
*A61F 13/51* (2006.01)

(52) U.S. Cl.
CPC ...... *A61F 13/475* (2013.01); *A61F 13/49007* (2013.01); *A61F 13/51* (2013.01)

(58) Field of Classification Search
CPC .......... A61F 13/475; A61F 2013/49493; A61F 13/49413; A61F 13/49466
See application file for complete search history.

(56) References Cited

U.S. PATENT DOCUMENTS 6,258,076 B1 * 7/2001 Glaug .................... A61F 13/532
604/386
2002/0183706 A1 * 12/2002 Valentin ............ A61F 13/49466
604/394

(Continued)

FOREIGN PATENT DOCUMENTS

JP        2003-199788 A      7/2003
JP        2016-067761 A      5/2016

(Continued)

OTHER PUBLICATIONS

Office Action issued in counterpart Chinese Patent Application No. CN 201911240796.7 issued Apr. 21, 2022, with translation (15 pages).

(Continued)

*Primary Examiner* — Susan S Su
*Assistant Examiner* — Katherine-Ph Minh Pham
(74) *Attorney, Agent, or Firm* — Osha Bergman Watanabe & Burton LLP

(57) ABSTRACT

A disposable diaper having a front-rear direction and a width direction includes: a first waistline region; a second waistline region; a crotch; an absorbent core; a waistband; a body portion disposed on a non-skin facing surface side of the waistband; and a space that opens toward the crotch region disposed on the non-skin facing surface side of the waistband. The body portion includes a first outer end edge that is an outer end edge in the front-rear direction in the first waistline region. In a natural state of half fold in which the waistband is sandwiched by the body portion and the disposable diaper is folded at a fold line extending in the width direction as a base point in the crotch region, a part of the waistband protrudes from the first outer end edge in the front-rear direction.

11 Claims, 11 Drawing Sheets

(56) References Cited

U.S. PATENT DOCUMENTS

| | | | |
|---|---|---|---|
| 2009/0062763 A1* | 3/2009 | Hancock-Cooke | ............................ A61F 13/49466 604/385.24 |
| 2013/0090623 A1* | 4/2013 | Ohashi | .................. A61F 13/493 604/389 |
| 2018/0071155 A1 | 3/2018 | Bishop et al. | |

FOREIGN PATENT DOCUMENTS

| | | | | |
|---|---|---|---|---|
| JP | 2017-099854 A | | 6/2017 | |
| WO | WO-2016051938 A1 * | | 4/2016 | ............. A61F 13/15 |

OTHER PUBLICATIONS

Office Action issued in counterpart Japanese Patent Application No. JP 2018-230409 mailed Apr. 5, 2022, with translation (9 pages).
International Search Report issued in corresponding International Application No. PCT/JP2019/047736 mailed Mar. 10, 2020 (5 pages).
Written Opinion of the International Searching Authority issued in corresponding International Application No. PCT/JP2019/047736 mailed Mar. 10, 2020 (4 pages).
Office Action issued in counterpart Korean Patent Application No. 10-2021-7017245 mailed Apr. 11, 2024, with translation (12 pages).

\* cited by examiner

DISPOSABLE DIAPER

BACKGROUND

Technical Field

The present invention generally relates to a disposable diaper having a waistband.

Related Art

Conventionally, disposable diapers having a waistband arranged in the waistline region are known (for example, refer to Patent Literature 1). The waistband forms a space that opens toward the crotch region. The waistband is arranged at least on the non-skin facing surface side of the space, functioning as a pocket that accommodates excrement moving toward the waist opening. With this configuration, it is possible to suppress the leakage of excrement through the waist opening.

PATENT LITERATURE

Patent Literature 1: US Patent Publication No. 2018/71155

Typical disposable diapers having no waistband are broadly known compared with disposable diapers having a waistband. Therefore, there is a case where a wearing helper puts a disposable diaper having a waistband on a wearer in the same manner as typical disposable diapers without recognizing the waistband. Therefore, there is a risk that the wearing helper may use the disposable diaper with a concern of leakage through the waist opening as in typical disposable diapers in spite of the presence of the waistband in the disposable diaper worn on the wearer.

In addition, since the wearing helper does not recognize the waistband at the time of putting the disposable diaper on the wearer, there is a risk that the disposable diaper is worn in a state in which the waistband is inappropriately bent. In this case, it is not possible to sufficiently form a space to be functioning as a pocket, which is more likely to cause excrement to leak through the waist opening.

SUMMARY

One or more embodiments provide a disposable diaper including a waistband which reduces a concern of the leakage of excrement through the waist opening and easily makes wearing helpers feel secure.

A disposable diaper according to one or more embodiments has a front-rear direction and a width direction that are orthogonal to each other, a first waistline region, a second waistline region, and a crotch region arranged between the first waistline region and the second waistline region, an absorbent core, a waistband arranged in the first waistline region, and a body portion that includes the absorbent core and is formed of a member that is arranged on a non-skin facing surface side of the waistband. A space that opens toward the crotch region is formed on the non-skin facing surface side of the waistband. The disposable diaper has the body portion that includes the absorbent core and is formed of a member that is arranged on the non-skin facing surface side of the waistband. The body portion has a first outer end edge that is an outer end edge in the front-rear direction in the first waistline region. In a natural state of half fold in which the disposable diaper is folded at a fold line extending in the width direction as a base point in the crotch region such that the waistband is sandwiched by the body portion, a part of the waistband is exposed on an outer side of the first outer end edge in the front-rear direction.

DETAILED DESCRIPTION

(1) Outline of Embodiments

Figure 1:
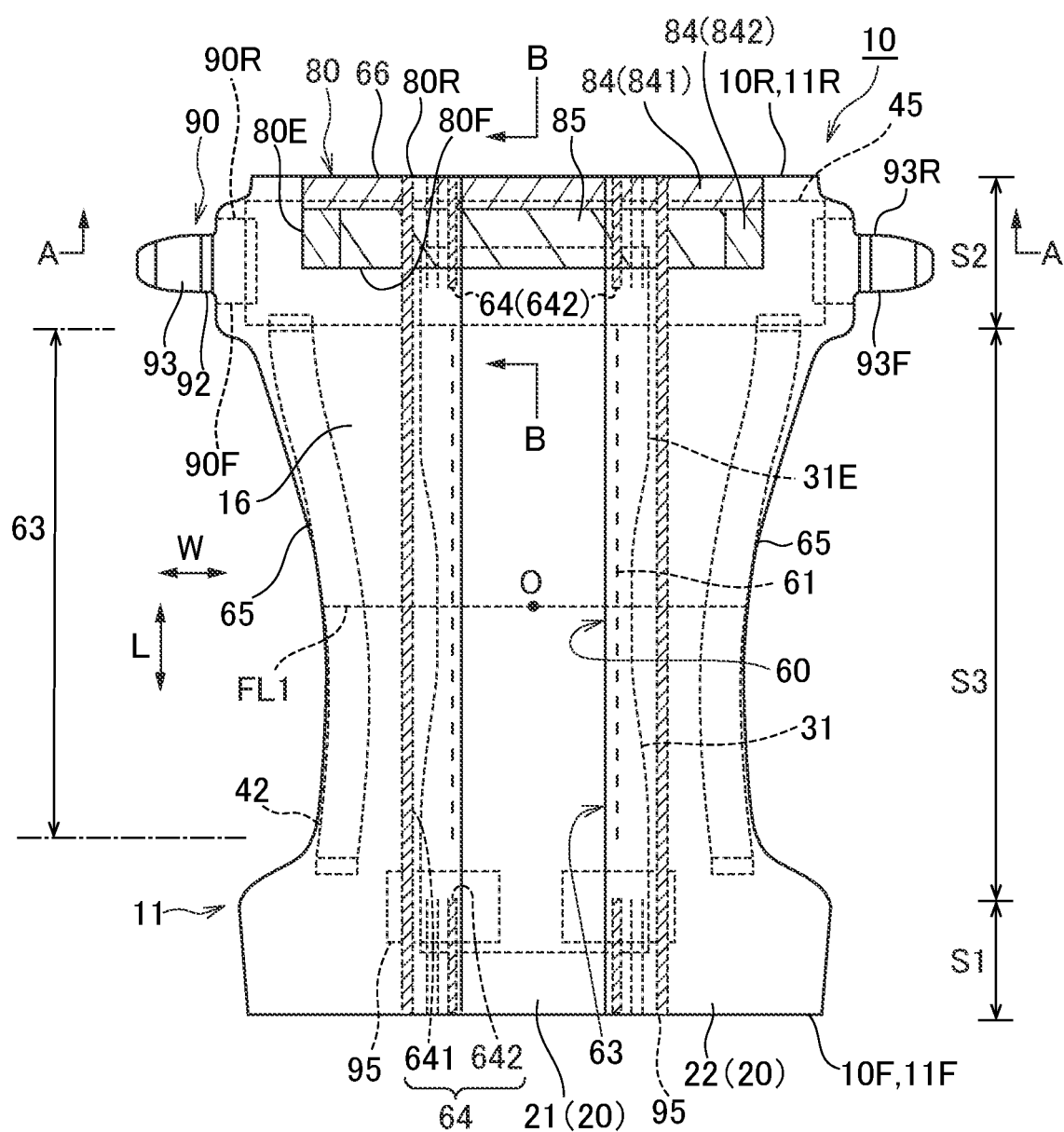
FIG. 1 is a schematic plan view of a disposable diaper according to one or more embodiments as viewed from a skin facing surface side.

Embodiments of the present invention will be described below with reference to the drawings. A disposable diaper according to one or more embodiments has a front-rear direction and a width direction that are orthogonal to each other, a first waistline region, a second waistline region, and a crotch region arranged between the first waistline region and the second waistline region, an absorbent core, a waistband arranged in the first waistline region, and a body portion that includes the absorbent core and is formed of a member that is arranged on a non-skin facing surface side of the waistband. A space that opens toward the crotch region is formed on the non-skin facing surface side of the waistband. The disposable diaper has the body portion that includes the absorbent core and is formed of a member that is arranged on the non-skin facing surface side of the waistband. The body portion has a first outer end edge that is an outer end edge in the front-rear direction in the first waistline region. In a natural state of half fold in which the disposable diaper is folded at a fold line extending in the width direction as a base point in the crotch region such that the waistband is sandwiched by the body portion, a part of the waistband is exposed on an outer side of the first outer end edge in the front-rear direction. In other words, in the natural state, a part of the waistband may protrude from the first outer end edge in the front-rear direction.

Typically, disposable diapers are in a natural state of half fold as a pre-use state so as not to be bulky before use. According to one or more embodiments, in such a natural state of half fold, a part of the waistband is exposed on the outer side of the first outer end edge in the front-rear direction. For a wearing helper, even before the use of the disposable diaper, in a plan view of the disposable diaper viewed from the first waistline region side, it is possible to visually recognize the part of the waistband that is exposed from the body portion, and it becomes easy to recognize the waistband. Once the wearing helper recognizes the waistband, it is possible to reduce a concern of the leakage of excrement through the waist opening and to make the wearing helper feel secure. In addition, in a case where the wearing helper recognizes the waistband, it becomes easy to find out that the waistband is in an inappropriately bent state while the disposable diaper is being put on a wearer. In a case where the waistband is in an inappropriately bent state, the wearing helper is able to suppress the leakage of excrement through the waist opening by correcting the waistband into an appropriate state, and thus the wearing helper can be made to feel secure.

According to one or more embodiments, the body portion may have a second outer end edge that is an outer end edge in the front-rear direction in the second waistline region. In the natural state of half fold, a part of the waistband may be exposed on an outer side of the second outer end edge in the front-rear direction. In the natural state of half fold, since parts of the waistband are exposed on the outer sides in the front-rear direction of not only the first outer end edge but also the second outer end edge, it is possible to visually recognize the parts of the waistband not only from the side on which the first outer end edge is arranged but also from the side on which the second outer end edge is arranged. Therefore, for the wearing helper, even before the use of the disposable diaper, it becomes easier to visually recognize the parts of the waistband that are exposed from the body portion and to recognize the waistband.

According to one or more embodiments, the waistband may have a skin contact portion including a skin contact surface that comes into contact with a skin of a wearer. The skin contact portion that is not joined to the body portion may have an outer skin contact portion that is an outer side portion relative to a center of the skin contact portion in the front-rear direction and an inner skin contact portion that is an inner side portion relative to the center of the skin contact portion in the front-rear direction. A contractive force of the inner skin contact portion in the width direction may be greater than a contractive force of the outer skin contact portion in the width direction. Since the contractive force of the inner skin contact portion in the width direction is greater than the contractive force of the outer skin contact portion in the width direction, the inner skin contact portion contracts in the width direction more than the outer skin contact portion. With this configuration, the length of the inner skin contact portion in the width direction becomes shorter than the length of the outer skin contact portion in the width direction. Since the outer skin contact portion and the inner skin contact portion are the same skin contact portion, a portion of the outer skin contact portion close to the inner skin contact portion further contracts due to the contraction of the inner skin contact portion. On the other hand, a portion of the outer skin contact portion far from the inner skin contact portion is not easily affected by the contraction of the inner skin contact portion and is unlikely to contract due to the contraction of the inner skin contact portion. Therefore, the skin contact portion is likely to deform in an arc shape such that the center of the skin contact portion in the width direction protrudes toward the outer side in the front-rear direction. With this configuration, the center of the skin contact portion in the width direction is likely to protrude toward the outer side in the front-rear direction more than the end portions of the skin contact portion in the width direction. Even in a case where the end portions of the skin contact portion in the width direction are not exposed from the body portion, the center of the skin contact portion in the width direction is exposed from the body portion, and it becomes easy for the wearing helper to recognize the waistband.

According to a preferable aspect, the body portion may have a waist contraction region that is arranged at least in the first waistline region. The waist contraction region may extend in the width direction so as to straddle a center of the body portion in the width direction and may contract in the width direction. Due to the contraction of the waist contraction region, the body portion having the waist contraction region also contracts. Here, the inner side portion of the waist contraction region in the front-rear direction is arranged on the absorbent core side compared with the outer side portion of the waist contraction region in the front-rear direction. Therefore, in the region on the absorbent core and a region extended from the absorbent core in the front-rear direction, the inner side portion of the waist contraction region is unlikely to contract in the width direction compared with the outer side portion of the waist contraction region due to the stiffness of the absorbent core. With this configuration, the length in the width direction of the body portion that overlaps the outer side portion of the waist contraction region in the thickness direction is likely to become shorter than the length of the body portion that overlaps the inner side portion of the waist contraction region in the thickness direction, and the body portion deforms in an arc shape in the region extended from the absorbent core such that the center of the first outer end edge of the body portion in the width direction is recessed toward the inner side. Therefore, even in a case where the end portions of the waistband in the width direction are not exposed from the body portion, the center of the waistband in the width direction is exposed from the body portion, and it becomes easy for the wearing helper to recognize the waistband.

According to a preferable aspect, an inner end edge of the waist contraction region in the front-rear direction may overlap the absorbent core in the thickness direction. An overlapped portion in the inner side portion of the waist contraction region in the front-rear direction that overlaps the absorbent core is unlikely to contract in the width direction due to the stiffness of the absorbent core compared with the outer side portion of the waist contraction region in the front-rear direction. Therefore, the length in the width direction of the body portion that overlaps the overlapped portion of the waist contraction region in the thickness direction becomes longer than the length in the width direction of the body portion that overlaps the outer side portion of the waist contraction region in the thickness direction. Therefore, the body portion is more likely to deform in an arc shape in the region extended from the absorbent core such that the center of the first outer end edge of the body portion in the width direction is recessed toward the inner side. Therefore, even in a case where the end portions of the waistband in the width direction are not exposed from the body portion, the center of the waistband in the width direction is further exposed from the body portion, and it becomes easy for the wearing helper to recognize the waistband.

According to a preferable aspect, the waistband may have a pair of side joining portions that is positioned at both end portions of the waistband in the width direction and is joined to the body portion. Each of the pair of side joining portions is positioned on an outer side of an outer side edge of the absorbent core in the width direction. In a case where each of the pair of side joining portions is positioned on the outer side of the outer side edge of the absorbent core in the width direction, at least a part of each of the pair of side joining portions is positioned away from the region on the absorbent core and the region extended from the absorbent core in the front-rear direction. Therefore, even when the body portion deforms in an arc shape in the region extended from the absorbent core such that the center of the first outer end edge of the body portion in the width direction is recessed toward the inner side, at least a part of the side joining portion that is positioned away from the region on the extended portion is not affected by the deformation of the body portion. With this configuration, it is possible to suppress the center of the waistband in the width direction being recessed toward the inner side and to suppress a decrease in the amount of the waistband exposed from the body portion. By suppressing the reduction in the amount of exposure of the waistband, the wearer can easily see a part of the waistband even before using the disposable diaper, and can easily recognize the waistband.

According to a preferable aspect, the body portion may have a skin surface side sheet that is positioned on a skin facing surface side of the absorbent core. The skin surface side sheet may have a top-surface sheet and a pair of side sheets that covers both outer side portions of the top-surface sheet. Each of the pair of side sheets may configure a leak-proof gather having a contraction portion that rises due to contraction of a leak-proof elastic member that extends in the front-rear direction. The waistband may have a pair of side joining portions that is positioned at both end portions of the waistband in the width direction and is joined to the body portion. Each of the pair of side joining portions may be positioned on an outer side of the leak-proof elastic member in the width direction. Since each of the pair of side joining portions is positioned on the outer side of the leak-proof elastic member in the width direction, the pair of side joining portions is unlikely to be directly affected by the contraction of the leak-proof elastic member. With this configuration, it becomes difficult for the waistband to be pulled toward the inner side in the front-rear direction, and it is possible to suppress a decrease in the amount of the waistband exposed from the body portion. By suppressing the reduction in the amount of exposure of the waistband, the wearer can easily see a part of the waistband even before using the disposable diaper, and can easily recognize the waistband.

According to a preferable aspect, the leak-proof gather has a base end edge that acts as a rising fulcrum of the contraction portion on an outer side of the contraction portion in the width direction. Each of the pair of side joining portions may be positioned on an outer side of the base end edge in the width direction. Since each of the pair of side joining portions is positioned on the outer side of the base end edge in the width direction, the pair of side joining portions is unlikely to be affected by the contraction of the contraction portion. With this configuration, it becomes difficult for the waistband to be pulled toward the inner side in the front-rear direction, and it is possible to suppress a decrease in the amount of the waistband exposed from the body portion. Even before the use of the disposable diaper, it becomes easy for the wearing helper to visually recognize a part of the waistband and to recognize the waistband.

According to a preferable aspect, the waistband may have a joining portion joined to the body portion and a non-joining portion that is not joined to the body portion. The non-joining portion may be folded back to an outer side in the front-rear direction at a band fold line extending in the width direction as a base point. The non-joining portion may have a rising portion that extends from the joining portion to the band fold line and is capable of rising and a folded-back portion that extends from the band fold line toward the outer side in the front-rear direction and is positioned on a skin facing surface side of the rising portion. A total length of a length from one end edge to the other end edge of the rising portion in the front-rear direction and a length from one end edge to the other end edge of the folded-back portion in the front-rear direction may be longer than a length from a boundary between the joining portion and the rising portion to the first outer end edge. Since the folded-back portion comes close to the wearing helper due to the rising of the rising portion at the time of putting the disposable diaper on the wearer, for the wearing helper, it is possible to visually recognize the waistband three-dimensionally, and it becomes easy to recognize the waistband.

In addition, since the total length of the rising portion and the folded-back portion is longer than the length from the boundary between the joining portion and the rising portion to the first outer end edge, it becomes easy for the folded-back portion to be positioned on the outer side of the body portion in the front-rear direction due to the rising of the rising portion. In a case where the folded-back portion is positioned on the outer side of the body portion in the front-rear direction, a part of the waistband does not overlap the body portion 11, and thus the visibility of the waistband is enhanced, and it becomes easy for the wearing helper to recognize the waistband.

According to a preferable aspect, the length from the one end edge to the other end edge of the rising portion in the front-rear direction may be longer than the length from the boundary between the joining portion and the rising portion to the first outer end edge. Since the length of the rising portion is longer than the length from the boundary between the joining portion and the rising portion to the first outer end edge, due to the rising of the rising portion, the folded-back portion comes closer to the wearing helper, and it becomes easier to recognize the waistband. In addition, compared with a case where the length of the rising portion is short, the distance that the folded-back portion moves toward the outer side in the front-rear direction due to the rising of the rising portion becomes long, and it becomes easier for the folded-back portion to be positioned on the outer side of the body portion in the front-rear direction. In a case where the folded-back portion is positioned on the outer side of the body portion in the front-rear direction, the visibility of the waistband is enhanced, and it becomes easy for the wearing helper to recognize the waistband.

(2) Overall Configuration of Disposable Diaper

Hereinafter, a disposable diaper according to one or more embodiments will be described with reference to the drawings. It should be noted that, in the following description of the drawings, identical or similar portions will be given identical or similar reference signs. Here, the drawings are schematic views, and attention needs to be paid to the fact that the ratios between individual dimensions and the like are different from actual ones. Therefore, specific dimensions and the like need to be determined with reference to the following description. In addition, there may be parts in which the relations and ratios of the dimensions of the drawings are different from each other.

Figure 2:
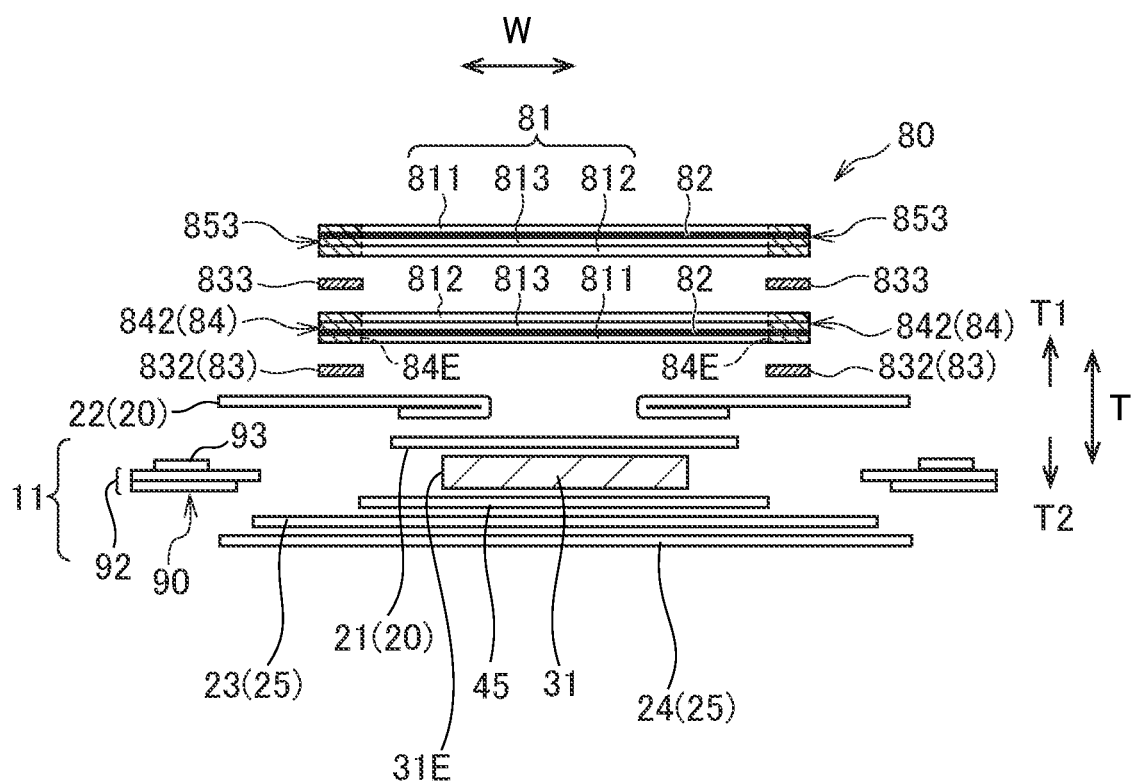
FIG. 2 is a schematic cross-sectional view taken along a line A-A shown in FIG. 1.
Figure 3:
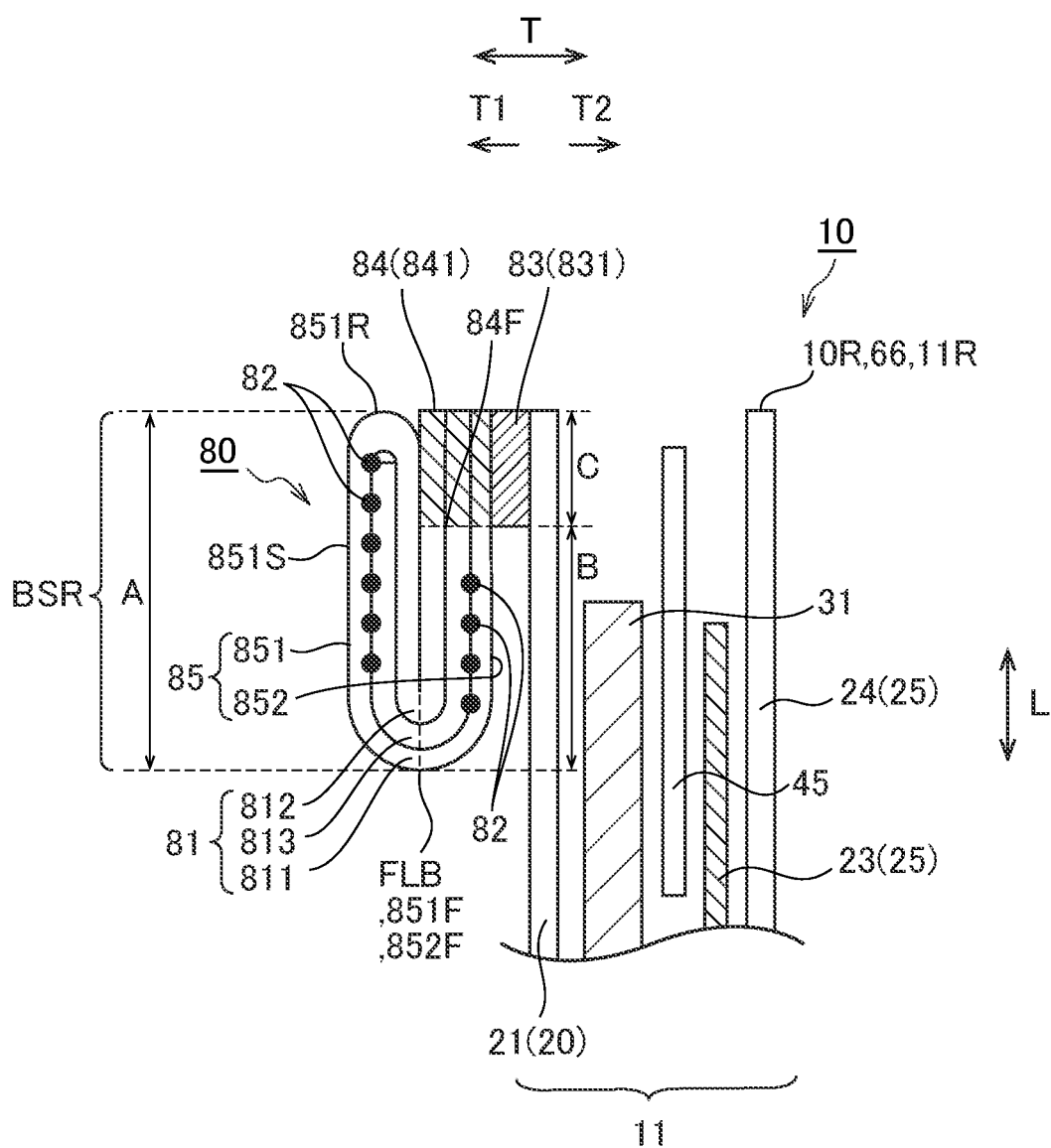
FIG. 3 is a schematic cross-sectional view taken along a line B-B shown in FIG. 1 in a stretched state.
Figure 4:
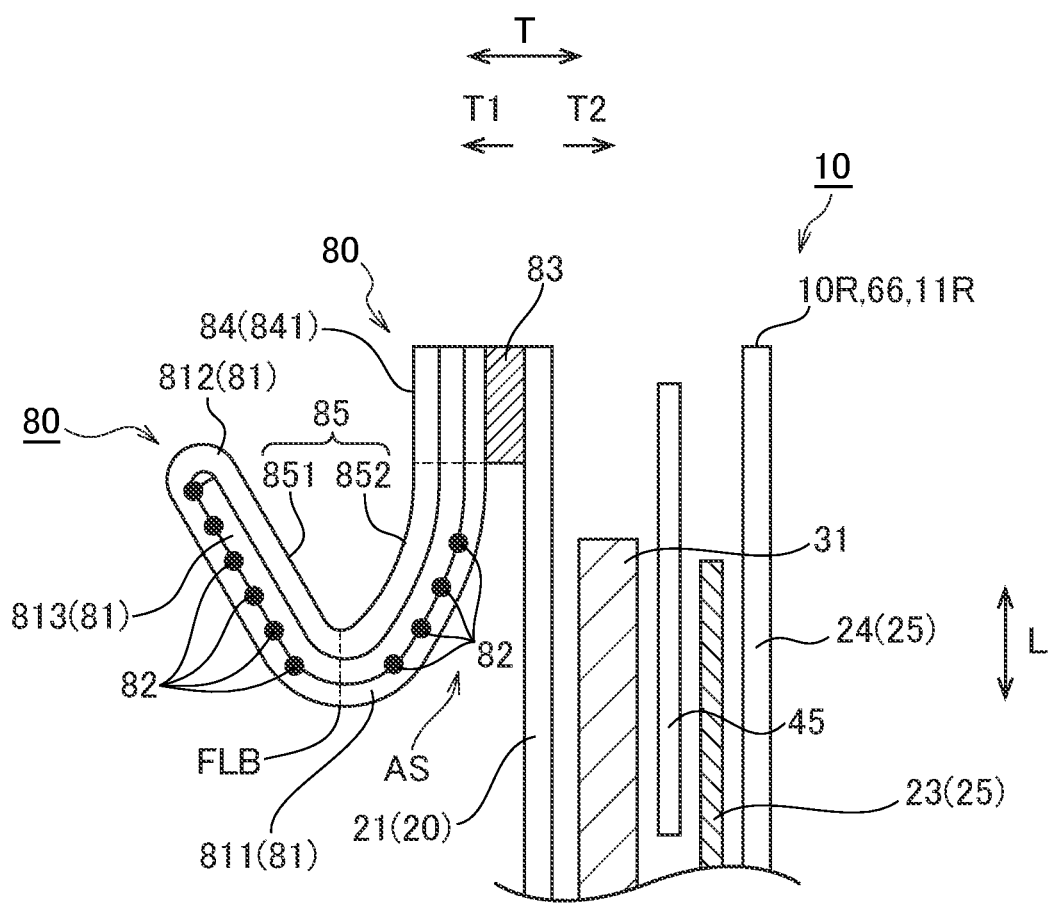
FIG. 4 is a schematic cross-sectional view taken along a line B-B shown in FIG. 1 in a natural state.
Figure 5:
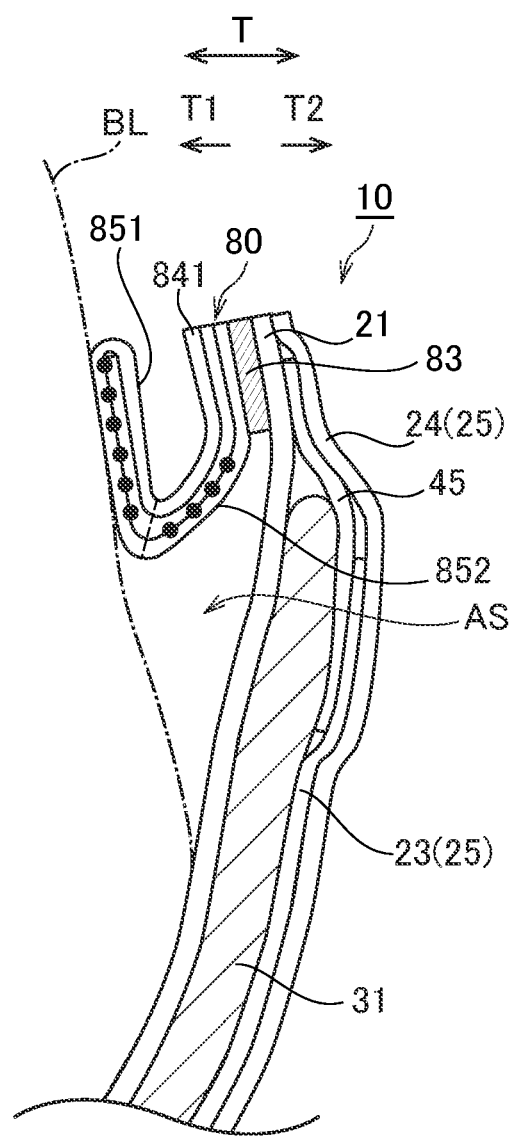
FIG. 5 is a view schematically showing a FIG. 4-based cross section in a worn state.

The disposable diaper is a tape-type disposable diaper. FIG. 1 is a schematic plan view of a disposable diaper 10 according to one or more embodiments as viewed from the skin facing surface side. FIG. 2 is a schematic cross-sectional view of the disposable diaper shown in FIG. 1 taken along the line A-A. In the schematic cross-sectional view shown in FIG. 2, for convenience of description, individual members are shown to be separated from each other in a thickness direction T, but are in contact with each other in the thickness direction T in actual products. FIG. 1 and FIG. 2 show the disposable diaper in a stretched state. In one or more embodiments, the stretched state is a state in which the disposable diaper 10 is stretched to a state in which wrinkles are not formed. In one or more embodiments, the natural state means that, in the case of the disposable diaper 10 housed in the package, the disposable diaper 10 is taken out from the package, and the atmosphere is kept at 20° C.±2° C. and a relative humidity of 60%±5% RH. It is in a state of being left for 24 hours. FIG. 3 is a schematic cross-sectional view taken along a line B-B shown in FIG. 1 in a stretched state. FIG. 4 is a schematic cross-sectional view taken along a line B-B shown in FIG. 1 in a natural state. FIG. 5 is a view showing a worn state based on the cross section shown in FIG. 4. BL shown in FIG. 5 indicates the body line of a wearer.

The disposable diaper 10 has a front-back direction L and a width direction W orthogonal to each other. The front-back direction L is defined by a direction extending toward the body front side and the body back side. In other words, the front-back direction L refers to a direction in which an unfolded disposable diaper 10 extends forward and backward. Further, the disposable diaper 10 has a thickness direction T orthogonal to both the front-rear direction L and the width direction W. The thickness direction T extends toward a skin facing surface side T1 that is directed toward the wearer and a non-skin facing surface side T2 that is opposite to the skin facing surface side T1.

The disposable diaper 10 has a front waistline region S1, a rear waistline region S2, and a crotch region S3. The front waistline region S1 is a region that faces the front waistline (abdomen) of the wearer. The rear waistline region S2 is a region that faces the rear waistline (back portion) of the wearer and includes a region on which the body (buttocks) is placed when the disposable diaper 10 is put on. The crotch region S3 is a region located at the crotch of the wearer and arranged between the front waistline region S1 and the rear waistline region S2. Therefore, the crotch region S3 is arranged between the two waistline regions made up of the front waistline region S1 and the rear waistline region S2. The crotch region S3 is a region in which leg openings 65 arranged around the legs of the wearer are provided. The leg openings 65 are portions that are recessed toward the inner side in the width direction from the outer side edges of the disposable diaper 10.

The disposable diaper 10 includes a body portion 11 and a waistband 80 described below. The body portion 11 is formed of members that are arranged on the non-skin facing surface side T2 of the waistband 80. Therefore, the body portion 11 is formed of, out of members that constitute the disposable diaper 10, members except the waistband 80. The body portion 11 includes an absorbent core 31 described below.

The body portion 11 has a front end edge 11F that is the outer end edge on an outer side (front side) in the front-rear direction L in the front waistline region S1 and a rear end edge 11R that is the outer end edge on an outer side (rear side) in the front-rear direction L in the rear waistline region S2. The front end edge 11F may be a second outer end edge, and the rear end edge 11R may be a first outer end edge.

The disposable diaper 10 includes the absorbent core 31 containing an absorbent material. The absorbent core 31 comprises an absorbent material such as ground pulp or super absorbent polymer (SAP), or a mixture thereof. The absorbent core 31 may be covered with a core wrap (not shown). The absorbent core 31 and the core wrap may constitute an absorbent body. The core wrap is made of a tissue or SMS non-woven fabric, and may be arranged on the skin facing surface side T1 of the absorbent core 31 and the non-skin facing surface side T2 of the absorbent core 31.

As shown in FIG. 2, the disposable diaper 10 has a skin surface side sheet 20 positioned on the skin facing surface side T1 of the absorbent core 31. The skin-side sheet 20 covers the absorbent core 31 and is arranged over the entire disposable diaper 10. The skin surface side sheet 20 of one or more embodiments includes a top-surface sheet 21 and a pair of side sheets 22. It should be noted that, in the disposable diaper having the core wrap, the skin surface side sheet 20 is a sheet that is positioned on the skin facing surface side T1 of the core wrap. The top-surface sheet 21 may be disposed across the center of the absorbent core 31 in the width direction W. The pair of side sheets 22 may be arranged so as to cover both outer side portions of the top-surface sheet 21. The top-surface sheet 21 and the side sheets 22 may be made of a liquid-permeable sheet such as a nonwoven fabric or a perforated plastic film.

The inner side portion of the side sheet 22 may be folded back and overlapped. Between the doubled portions of the side sheet 22, a leak-proof elastic member 61 extending in the front-rear direction L may be provided. The leak-proof elastic member 61 stretches and contracts in the front-rear direction L. The leak-proof elastic member 61 may be formed of an elastic string that stretches and contracts in the front-rear direction L. The side sheet 22 rises toward the skin facing surface side T1 due to the contraction of the leak-proof elastic member 61. The pair of side sheets 22 configures a leak-proof gather 60. The leak-proof gather 60 has a contraction portion 63 that rises due to the contraction of the leak-proof elastic member 61. The leak-proof gather 60 has leak-proof base end edges 64 that serve as the rising fulcrums of the contraction portion 63. The leak-proof base end edge 64 has a first leak-proof base end edge 641 and a second leak-proof base end edge 642.

The first leak-proof base end edges 641 serve as the rising fulcrums of the contraction portion 63 on the outer sides of the contraction portion 63 in the width direction W. The first leak-proof base end edges 641 are the inner side edges of regions in which the side sheet 22 and the top-surface sheet 21 are joined to each other on the outer sides of the contraction portion 63 in the width direction. The second leak-proof base end edges 642 serve as the rising fulcrums of the contraction portion 63 on both outer sides of the contraction portion 63 in the front-rear direction L. The second leak-proof base end edges 642 are the inner end edges of regions in which the side sheet 22 and the top-surface sheet 21 are joined to each other on both outer sides of the contraction portion 63 in the front-rear direction L. In the contraction portion 63, the side sheets 22 are not joined to the top-surface sheet 21, and the contraction portion 63 is a portion that is contractible due to the leak-proof elastic members 61 and does not include any portion in which the leak-proof elastic member 61 in a non-stretched state is arranged. The range of the contraction portion 63 in the front-rear direction is shown in FIG. 1.

Here, the outer side portion may be a portion occupying a certain range in the width direction W including the outer side edge in the width direction W, and the outer side edge is the outer side edge in the width direction W. In addition, the inner portion is a portion that occupies a certain range in the width direction W including an inner edge in the width direction W, and the inner edge is an inner edge in the width direction W.

The disposable diaper 10 has a non-skin surface side sheet 25 positioned on the non-skin facing surface side T2 of the absorbent core 31. The non-skin surface side sheet 25 covers the absorbent core 31 and is arranged throughout the entire disposable diaper 10. The non-skin surface side sheet 25 according to one or more embodiments includes a back-surface sheet 23 and an exterior sheet 24. It should be noted that, in the disposable diaper having the core wrap, the non-skin surface side sheet 25 is a sheet that is positioned on the non-skin facing surface side T2 of the core wrap. The back-surface sheet 23 is a liquid-impermeable sheet, and it is possible to use a polyethylene sheet, a laminated nonwoven fabric containing polypropylene or the like as a main component, a breathable resin film, a sheet obtained by joining a breathable resin film to nonwoven fabric such as spunbond or spunlace. The exterior sheet 24 may be provided on the non-skin facing surface side T2 of the back-surface sheet 23. The exterior sheet 24 may be made of liquid-permeable nonwoven fabric. The length of the back-surface sheet 23 in the width direction W is shorter than the length of the exterior sheet 24 in the width direction W, and the length of the back-surface sheet 23 in the front-rear direction L is shorter than the length of the exterior sheet 24 in the front-rear direction L. Good.

A fastening tape 90 is provided in the rear waistline region S2. The fastening tape 90 has a base portion 92 and a locking portion 93. At least a part of the base portion 92 is joined between the skin surface side sheet 20 and the non-skin surface side sheet 25 and extends toward the outer side in the width direction W from the skin surface side sheet 20 and the non-skin surface side sheet 25. The locking portion 93 is provided on the base portion 92 and is detachably fastened to a target portion 95 (refer to FIG. 1). The fastening tapes 90 extend along the width direction W in the back waistline region S2 and are fastened to the target portions 95, thereby holding the disposable diaper 10 on the wearer's body. The target portions 95 are arranged in the front waistline region S1 and are configured such that the fastening tapes 90 are respectively attached thereto.

The disposable diaper 10 has the waistband 80 arranged in at least one waistline region of the two waistline regions (the front waistline region S1 and the rear waistline region S2). In one or more embodiments, the waistband 80 is arranged in the rear waistline region S2. The rear waistline region S2 may be a first waistline region, and the front waistline region S1 may be a second waistline region. The waistband 80 is arranged on the skin facing surface side T1 of the body portion 11. The waistband 80 is arranged on the skin facing surface side T1 of the skin surface side sheet 20. The waistband 80 floats from the skin surface side sheet 20 while the disposable diaper is worn. Therefore, a space that opens toward the crotch region S3 (an accommodation space AS in FIG. 4 and FIG. 5) is formed. The accommodation space AS is provided on the non-skin facing surface side of the waistband 80 and opens toward the crotch region. The waistband 80 is arranged at least on the skin facing surface side T1 of the accommodation space AS. In one or more embodiments, the waistband 80 is arranged on the skin facing surface side T1 of the accommodation space AS, and the body portion 11 (skin surface side sheet 20) is arranged on the non-skin facing surface side T2 of the accommodation space AS. The accommodation space AS functions as a pocket that accommodates excrement that moves toward the waist opening 66. Therefore, it is possible to suppress the leakage of excrement through the waist opening 66. The configuration of the waistband 80 will be described in detail later. The waist opening 66 is made up of a rear end edge 10R and a front end edge 10F of the disposable diaper 10 and is a portion in which the fastening tapes 90 surround the waistline in a state of being fastened to the target portions 95.

As shown in FIG. 1, a leg-around elastic member 42 that extends in the front-rear direction L may be provided between the side sheet 22 and the back-surface sheet 23 or between the side sheet 22 and the exterior sheet 24. The leg-around elastic members 42 may be configured by a belt-shaped elastic sheet that expands and contracts in the front-rear direction L. Due to the contraction of the leg-around elastic members 42, the disposable diaper 10 fits around the legs while worn. The leg-around elastic members 42 are arranged along the leg openings 65 at least in the crotch region S3 outside the absorbent core 31 in the width direction W.

A waist-around elastic member 45 that extends in the width direction W may be provided between the side sheets 22 and the back-surface sheet 23 and between the side sheets 22 and the exterior sheet 24. The waist-around elastic member 45 may be configured by a substantially rectangular elastic sheet that expands and contracts in the width direction W. The waist-around elastic member 45 is joined between the skin-side sheet 20 and the non-skin surface side sheet 25. For example, as shown in FIG. 2, the waist-around elastic member 45 is joined between the absorbent core 31 and the non-skin surface side sheet 25 or between the skin surface side sheet 20 and the non-skin surface side sheet 25 in a state of being stretched in the width direction W. By contraction of the waist-around elastic member 45, the disposable diaper 10 fits around the waist when worn. The waist-around elastic members 45 are arranged at least in the rear waistline region S2. In one or more embodiments, the waist-around elastic member 45 overlaps the absorbent core 31 in the thickness direction T. Therefore, a front end edge 45F of the waist-around elastic member 45 is positioned on the front side of the rear end edge of the absorbent core 31, and a rear end edge 45R of the waist-around elastic member 45 is positioned on the rear side of the front end edge of the absorbent core 31. The disposable diaper 10 has side flaps 16 that extend toward the outer side in the width direction W from outer side edges 31E of the absorbent core 31. The side flap 16 includes the fastening tape 90.

(3) Waistband Configuration

Next, the configuration of the waistband 80 will be described in detail. As shown in FIG. 3 to FIG. 5, the waistband 80 may have a sheet layer 81 in which a plurality of sheets is laminated together and band elastic members 82 joined to the sheet layer 81. The sheet layer 81 in the waistband 80 according to one or more embodiments may include a first nonwoven fabric layer 811, a second nonwoven fabric layer 812, and a film layer 813 arranged between the first nonwoven fabric layer 811 and the second nonwoven fabric layer 812. The first nonwoven fabric layer 811 and the second nonwoven fabric layer 812 are configured by folding back the same nonwoven fabric. The first nonwoven fabric layer 811 is located closest to the skin side sheet 20 side in the waistband 80.

The band elastic member 82 stretches and contracts in the width direction W. The band elastic members 82 are formed of a thread-shaped or band-shaped elastic member and are fixed to the sheet layer 81 in a state of being stretched in the width direction W. The band elastic members 82 are fixed between the first nonwoven fabric layer 811 and the liquid-impermeable film layer 813. A plurality of band elastic members 82 are arranged at intervals in the front-rear direction L. A plurality of the band elastic members 82 may be arranged in a skin contact portion 851 and a rising portion 852 described below, respectively.

The waistband 80 is configured to be stretchable in the width direction W. The waistband 80 may be configured so as to stretch and contract in the width direction due to the band elastic members 82 or may be configured to stretch and contract in the width direction due to the stretchability of the sheet layer 81. The waistband 80 has a band stretch/contraction region BSR that stretches and contracts in the width direction W (refer to FIG. 3). The band stretch/contraction region BSR is a region in the waistband 80 that stretches and contracts in the width direction W.

The waistband 80 may be arranged near the waist opening 66 in the back waistline region S2. Outer side edges 80E of the waistband 80 may be positioned on the outer sides of the outer side edges 31E of the absorbent core 31 in the width direction W and may be positioned on the inner sides of the inner side edges of the fastening tapes 90 in the width direction W. The front end edge 80F of the waistband 80 may be located rearward of the front end edge 90F of the fastening tape 90.

As shown in FIG. 3 to FIG. 5, the waistband 80 is joined to the body portion 11 (more specifically, the skin surface side sheet 20). As a method for joining the waistband 80, for example, a joining member such as a hot melt-type adhesive (HMA), a sonic seal, a heat seal, or the like is used. In one or more embodiments, the waistband 80 is joined by a joining member 83.

The joining member 83 has a first joining member 831 and second joining members 832. The first joining member 831 is arranged at an end portion of the waistband 80 in the front-rear direction L and extends in the width direction W (refer to FIG. 3). The second joining members 832 are arranged at the end portions of the waistband 80 in the width direction W and extend in the front-rear direction L (refer to FIG. 2).

The waistband 80 has a joining portion 84 joined to the body portion 11 and a non-joining portion 85 that is not joined to the body portion 11. The joining portion 84 is a portion that is in contact with the joining member 83 and is directly fixed to the body portion 11. The joining portion 84 has a first joining portion 841 and second joining portions 842. The first joining portion 841 is arranged at an end portion of the waistband 80 in the front-rear direction L and extends in the width direction W. In one or more embodiments, the first joining portion 841 is arranged on the rear side of the non-joining portion 85 (specifically, the rising portion 852). The first joining portion 841 is a portion that is in contact with the first joining member 831. The second joining portions 842 are a pair of side joining portions that is positioned at both end portions of the waistband 80 in the width direction W and is joined to the body portion 11. The second joining portions 842 extend in the front-rear direction L. The second joining portions 842 are arranged on the outer sides of the non-joining portion 85 in the width direction W (refer to FIG. 2). The second joining portions 842 are portions that are in contact with the second joining members 832. The non-joining portion 85 is a portion that is not in contact with the joining member 83, and it is possible to change the distance between the body portion 11 and the non-joining portion 85. The non-joining portion 85 has the skin contact portion 851 having a skin contact surface 851S that comes into contact with the skin of the wearer. As shown in FIG. 4 and FIG. 5, in one or more embodiments, a pocket that opens toward the front side is formed by the accommodation space AS sandwiched between the non-joining portion 85 of the waistband 80 and the skin surface side sheet 20. The skin contact portion 851 is arranged on the skin facing surface side T1 of the accommodation space AS.

The non-joining portion 85 may have the rising portion 852 that rises away from the body portion 11 (more specifically, the skin surface side sheet 20). In one or more embodiments, the non-joining portion 85 is folded back to the outer side in the front-rear direction L at a band fold line FLB as a base point. The skin contact portion 851 is formed from a portion in which the waistband 80 is folded back due to the band fold line FLB extending along the width direction W (folded-back portion). The skin contact portion (folded-back portion) 851 extends from the band fold line FLB toward the outer side (rear side) in the front-rear direction L and is positioned on the skin facing surface side T1 of the rising portion 852.

The rising portion 852 is formed of a portion in which the waistband 80 is not folded back due to the band fold line FLB. The rising portion 852 extends from the joining portion 84 to the band fold line FLB and is capable of rising. In one or more embodiments, the rising portion 852 is a portion of the non-joining portion 85 that does not come into contact with the skin of the wearer. It should be noted that, as shown in FIG. 3 to FIG. 5, the region that comes into contact with the skin of the wearer changes depending on the movement of the wearer and/or the rising status of the rising portion 852. Therefore, the length of the skin contact portion 851 in the front-rear direction L and the length of the rising portion 852 in the front-rear direction L may change.

Here, the length from one end edge (front end edge 851F) to the other end edge (rear end edge 851R) of the skin contact portion (folded-back portion) 851 in the front-rear direction L is represented by A. The length from one end edge (front end edge 852F) to the other end edge (rear end edge 852R) of the rising portion 852 in the front-rear direction L is represented by B. In this case, each of A and B may change depending on the movement of the wearer and/or the rising status of the rising portion 852. On the other hand, the total of A and B (A+B) is constant.

The length from the boundary between the joining portion 84 and the rising portion 852 to the rear end edge 11R of the body portion 11 is represented by C. In this case, the total length of A and B may be longer than the length C. That is, a condition "A+B>C" may be satisfied. When the wearing helper puts the disposable diaper 10 on the wearer, since the skin contact portion (folded-back portion) 851 comes close to the wearing helper due to the rising of the rising portion 852, for the wearing helper, it is possible to visually recognize the waistband 80 three-dimensionally, and it is easy to recognize the waistband 80. In addition, since the total length A+B of the rising portion 852 and the skin contact portion (folded-back portion) 851 is longer than the length C, it becomes easy for the skin contact portion (folded-back portion) 851 to be positioned on the outer side (rear side) of the body portion 11 in the front-rear direction L due to the rising of the rising portion 852. In this case, since a part of the waistband 80 does not overlap the body portion 11 in the rear waistline region S2 in the thickness direction T, the visibility of the waistband 80 is enhanced, and it becomes easy for the wearing helper to recognize the waistband 80. It should be noted that attention needs to be paid to the fact that, even in a case where the condition "A+B<C" is satisfied, a part of the waistband 80 can be exposed on the outer side of the rear end edge 11R in the front-rear direction L due to, for example, the deformation of the waistband 80 or the deformation of the body portion 11 which will be described below.

The length B of the rising portion 852 may be longer than the length C. That is, a condition "B>C" may be satisfied. Compared with a case where the length B of the rising portion 852 is short, the distance that the skin contact portion (folded-back portion) 851 moves toward the outer side (rear side) in the front-rear direction L due to the rising of the rising portion 852 becomes long, and it becomes easy for the skin contact portion (folded-back portion) 851 to be positioned on the outer side of the body portion 11 in the front-rear direction L. In a case where the skin contact portion (folded-back portion) 851 is positioned on the outer side of the body portion 11 in the front-rear direction L, since a part of the waistband 80 does not overlap the body portion 11 in the rear waistline region S2 in the thickness direction T, the visibility of the waistband 80 is enhanced, and it becomes easy for the wearing helper to recognize the waistband 80.

The rising portion 852 has the liquid-impermeable film layer 813. In one or more embodiments, the rising portion 852 is arranged on the skin facing surface side T1 of the accommodation space AS. Since the rising portion 852 having the liquid-impermeable film layer 813 is arranged on the skin facing surface side T1 of the accommodation space AS, it is possible to suppress excrement accommodated in the accommodation space AS that functions as a pocket oozing through the skin facing surface side T1 on which the film layer 813 is arranged. When the oozing of excrement after use is suppressed, it becomes easier to make the wearing helper feel secure about a concern of leakage.

The waistband 80 may have a base end edge that serves as a rising fulcrum of the rising portion 852. The base end edge has a first base end edge that is positioned on the waist opening 66 side of the rising portion 852 and second base end edges that are positioned on the outer sides of the absorbent core 31 in the width direction W. The first base end edge is formed of a front end edge 84F of the joining portion 84 (first joining portion 841). The joining portion 84 extends in the front-rear direction L from the first base end edge. The second base end edges are formed of side end edges 84E of the joining portion 84 (second joining portions 842).

It should be noted that, as shown in FIG. 2, the side end portions of the waistband 80 in the width direction W may be joined to each other with by side joining members 833 which are the joining member 83. The non-joining portion 85 may have a pair of skin contact joining portions 853 that is arranged on the skin facing surface side T1 of the side joining members 833. The non-skin facing surface side T2 of the pair of skin contact joining portions 853 is joined to the second joining portions 842 with the side joining members 833.

It should be noted that, as shown in FIG. 1, in a stretched state of the disposable diaper 10, the rear end edge 80R of the waistband 80 may be arranged on the rear side of rear end edges 93R of the locking portions 93 and may be arranged on the rear side of rear end edges 90R of the fastening tapes 90. Therefore, the waistband 80 is arranged on the waist opening 66 side, and thus it is possible to enhance the visibility of the waistband 80. In addition, the rear end edge 80R of the waistband 80 may be arranged on the rear side of the rear end edge of the absorbent core 31. Therefore, in a case where the absorbent core 31 fails to completely absorb excrement, it is possible to accommodate excrement that moves toward the rear side of the rear end edge of the absorbent core 31 in the accommodation space AS.

In addition, in a stretched state of the disposable diaper 10, the front end edge 80F of the waistband 80 may be arranged on the rear side of the front end edges 90F of the fastening tapes 90 and may be arranged on the rear side of front end edges 93F of the locking portions 93. Therefore, the waistband 80 does not become longer than necessary, and it is possible to suppress an increase in the material cost. In addition, the front end edge 80F of the waistband 80 may be arranged on the front side of the rear end edge of the absorbent core 31. Therefore, the beginning of the accommodation space AS is positioned on the front side of the rear end edge of the absorbent core, and thus it is possible to accommodate excrement that moves toward the rear side of the rear end edge of the absorbent core 31 in the accommodation space AS.

In addition, in a stretched state of the disposable diaper 10, the rear end edge 80R of the waistband 80 may overlap the body portion 11 in the rear waistline region S2 in the thickness direction T. Therefore, in a stretched state of the disposable diaper 10, the rear end edge 80R of the waistband 80 may not be arranged on the rear side of the rear end edge 11R of the body portion 11. The rear end edge 80R of the waistband 80 may be arranged on the front side (crotch region S3 side) of the rear end edge 11R of the body portion 11, and the rear end edge 80R of the waistband 80 and the rear end edge 11R of the body portion 11 may overlap each other in the thickness direction T. Therefore, it is possible to suppress a force directly acting on the waistband 80 during the conveyance of the disposable diaper 10 and to protect the waistband 80 before the use of the disposable diaper 10.

(4) Disposable Diaper 10 in Natural State of Half Fold

Figure 6A:
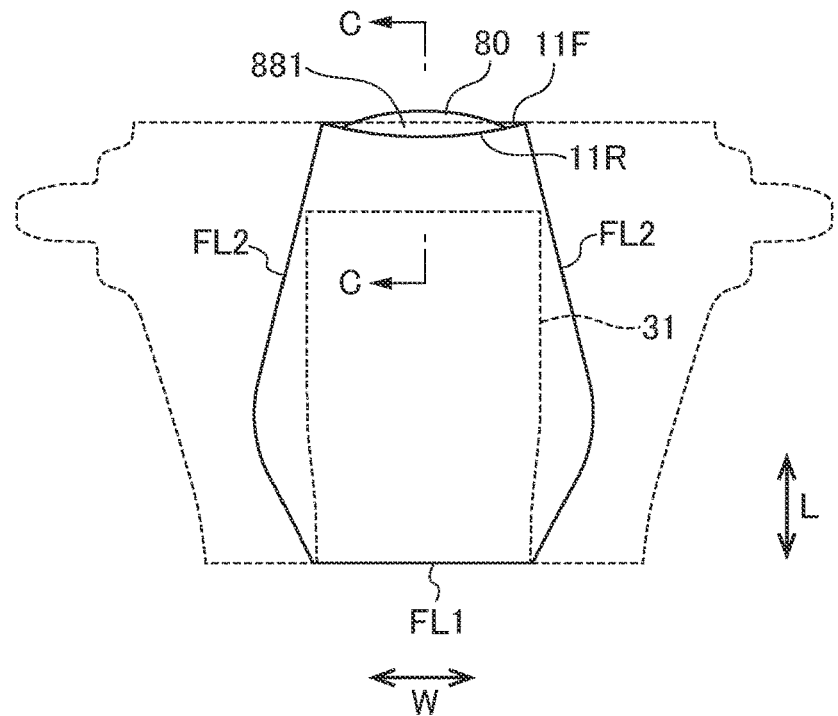
FIGS. 6A and 6B are schematic plan views of the disposable diaper 10 according to one or more embodiments in a natural state of half fold.
Figure 6B:
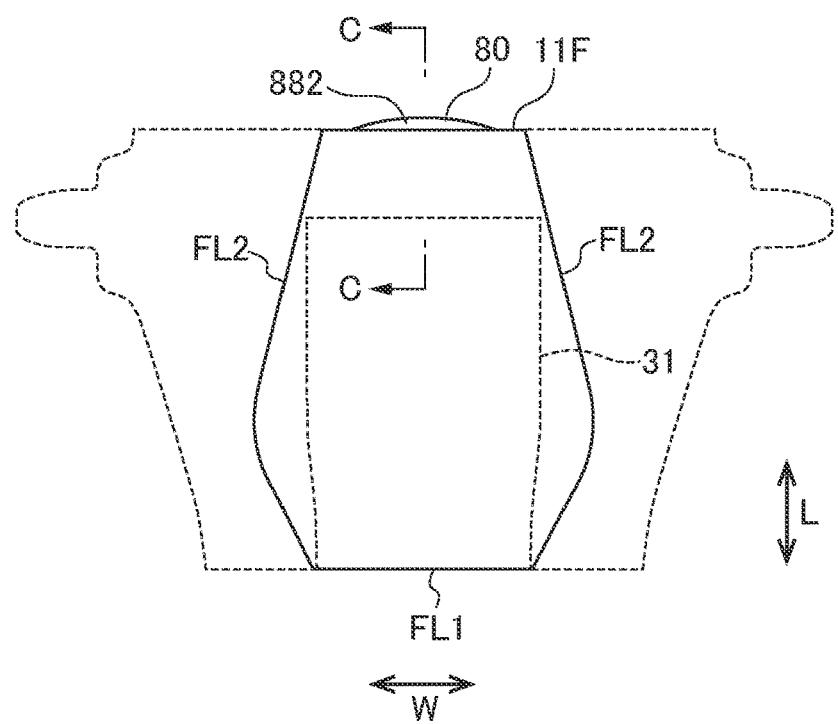
Figure 7:
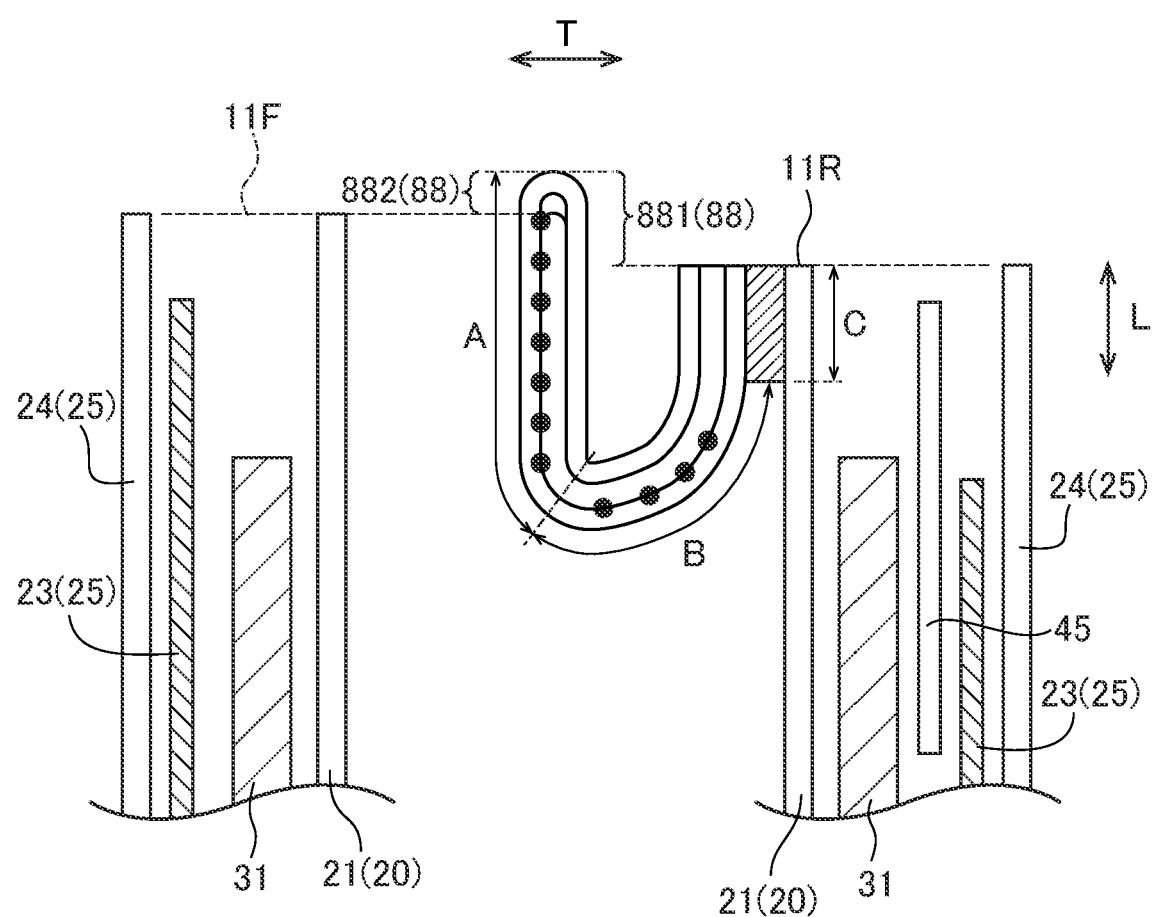
FIG. 7 is a schematic cross-sectional view taken along a line C-C of FIG. 6.
Figure 8A:
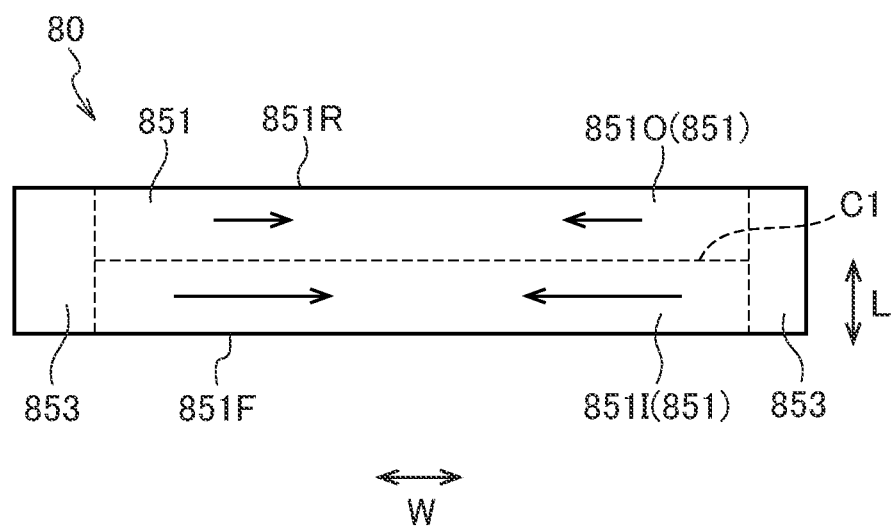
FIGS. 8A and 8B are schematic views for describing a waistband 80 according to one or more embodiments.
Figure 8B:
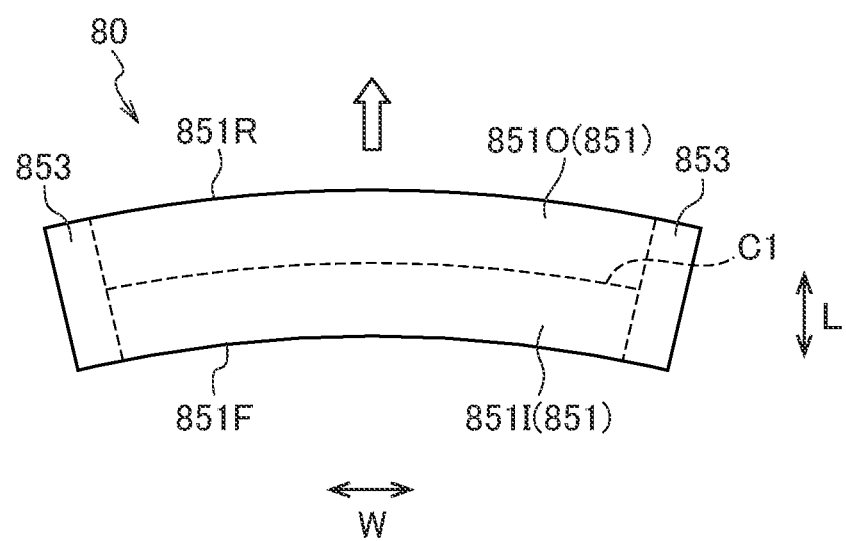
Figure 9A:
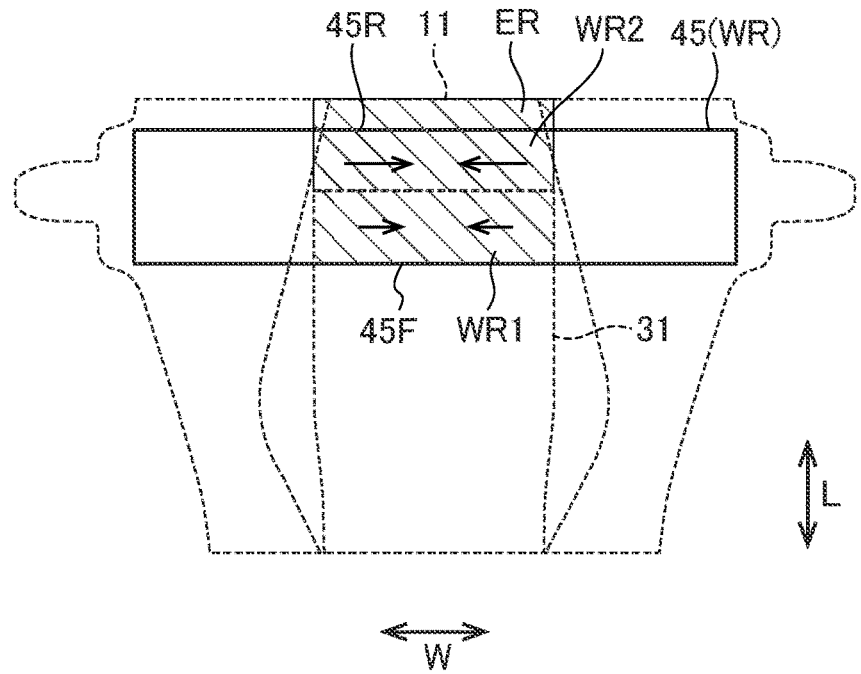
FIGS. 9A and 9B are schematic views for describing a waist-around elastic member 45.
Figure 9B:
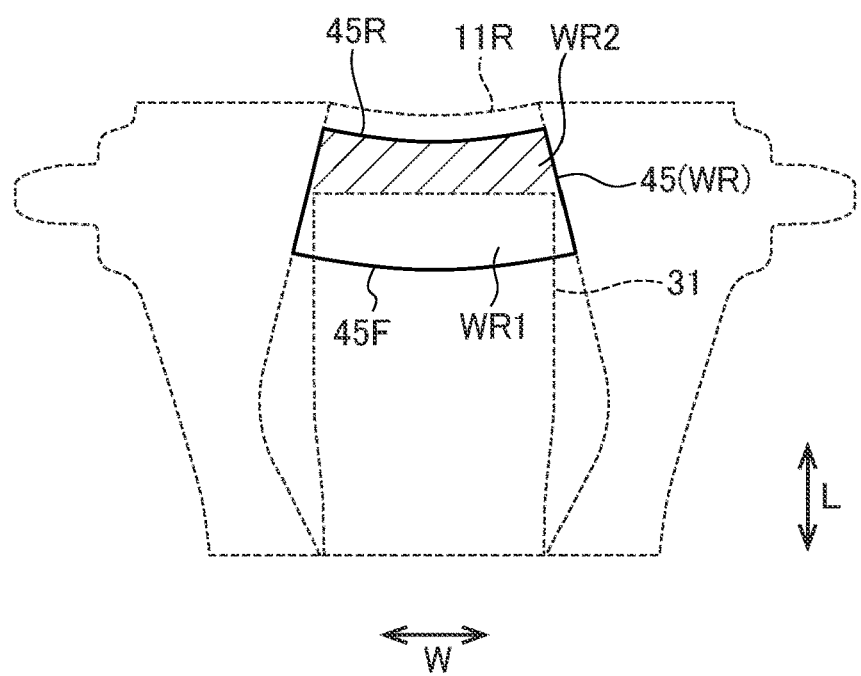

Next, the disposable diaper 10 in a natural state of half fold will be described using FIG. 6 to FIG. 9. FIG. 6 is a schematic plan view of the disposable diaper 10 according to one or more embodiments in a natural state of half fold. FIG. 6A is a schematic plan view of the disposable diaper 10 in a natural state of half fold as viewed from the rear waistline region S2 side. FIG. 6B is a schematic plan view of the disposable diaper 10 in the natural state of half fold as viewed from the front waistline region S1 side. FIG. 7 is a schematic cross-sectional view taken along a line C-C of FIG. 6. FIG. 8 is a schematic view for describing a waistband 80 according to one or more embodiments. FIG. 8A is a schematic plan view of the waistband 80 in a stretched state as viewed from the skin facing surface side T1. FIG. 8B is a schematic plan view of the waistband 80 in a natural state as viewed from the skin facing surface side T1. FIG. 9 is a schematic view for describing a waist-around elastic member 45. FIG. 9A is a schematic plan view of the waist-around elastic member 45 (waist contraction region WR) in a stretched state as viewed from the skin facing surface side T1. FIG. 9B is a schematic plan view of the waist-around elastic member 45 (waist contraction region WR) in a natural state of half fold as viewed from the skin facing surface side T1.

The disposable diaper 10 shown in FIG. 6 is in a natural state of half fold. The natural state of half fold is a state in which the disposable diaper 10 is folded at least at a first fold line as a base point such that the waistband 80 is sandwiched by the body portion 11. In one or more embodiments, the disposable diaper 10 in the natural state of half fold is in a state of being folded at a first fold line FL1 and second fold lines FL2 as base points.

The first fold line FL1 is a fold line extending along the width direction W and is a fold line arranged in the crotch region S3 (refer to FIG. 1). Typically, the first fold line FL1 is arranged in the vicinity of the center of the disposable diaper 10 in the front-rear direction L. When the disposable diaper 10 is folded at the first fold line FL1 as a base point, it is possible to approximately halve the length in the front-rear direction L. In one or more embodiments, the first fold line FL1 passes through the center O of the disposable diaper 10 in the front-rear direction L.

The second fold lines FL2 are fold lines extending from the end edges (the front end edge 10F and the rear end edge 10R) of the disposable diaper 10 in the front-rear direction L toward the crotch region. At least a part of the second fold line FL2 may be positioned on the outer side of the outer side edge 31E of the absorbent core 31 in the width direction W. The second fold line FL2 may be positioned on the inner side of the outer side edge 31E of the absorbent core 31 in the width direction W in the region on the outer sides of the end edges of the absorbent core 31 in the front-rear direction L. As shown in FIG. 6, in one or more embodiments, the second fold lines FL2 extend in the front-rear direction L, but may extend at an angle with respect to the front-rear direction L. In addition, as shown in FIG. 6, the second fold lines FL2 extend so as not to overlap the absorbent core 31 (absorbent body) in a plan view in the natural state of half fold. It should be noted that the second fold lines FL2 may overlap the absorbent core 31 (absorbent body) in a plan view in the natural state of half fold.

In addition, the second fold lines FL2 are fold lines for folding back (at least a part of) the side flaps 16. In the rear waistline region S2 in which the waistband 80 is arranged, when the disposable diaper 10 is folded at the second fold lines FL2 as base points, the side flaps 16 overlap the waistband 80 from the skin facing surface side T1.

Typically, the disposable diaper 10 before use is in a state of being folded at the first fold line FL1 and the second fold lines FL2 as base points so as not to be bulky. The disposable diaper 10 is folded at the second fold lines FL2 as base points and then folded at the first fold line FL1 as a base point. Therefore, the folded-back side flaps 16 are in a state of being sandwiched between the front waistline region S1 and the rear waistline region S2.

As shown in FIGS. 6A and 6B and FIG. 7, the waistband 80 has an exposed portion 88 that is exposed from the body portion 11 in the natural state of half fold. The exposed portion 88 is a portion of the waistband 80 that does not overlap the body portion 11 in the thickness direction T at least on one of the skin facing surface side T1 and the non-skin facing surface side T2 in the natural state of half fold. Therefore, the exposed portion 88 is a portion that is visually recognizable in the natural state of half fold.

As shown in FIG. 6A and FIG. 7, according to one or more embodiments, in the natural state of half fold, a part of the waistband 80 is exposed on the outer side of the rear end edge 11R of the body portion 11 in the front-rear direction L. In other words, in the natural state of half fold, a part of the waistband 80 protrudes from the rear end edge 11R of the body portion 11 in the front-rear direction L. Therefore, the waistband 80 has a first exposed portion 881 (exposed portion 88) that is exposed from the body portion 11 in the natural state of half fold. The first exposed portion 881 is a portion of the waistband 80 that is exposed on the outer side of the rear end edge 11R of the body portion 11 in the front-rear direction L in the natural state of half fold. Therefore, for the wearing helper, it is possible to visually recognize the part of the waistband 80 that is exposed from the body portion 11, and it becomes easy to recognize the waistband 80 in a plan view of the disposable diaper 10 as viewed from the rear waistline region S2 side even before the use of the disposable diaper 10. Once the wearing helper recognizes the waistband, it is possible to reduce a concern of the leakage of excrement through the waist opening 66 and to make the wearing helper feel secure about a concern of leakage. In addition, in a case where the wearing helper recognizes the waistband, it becomes easy to find out that the waistband 80 is in an inappropriately bent state when the disposable diaper 10 is put on a wearer. In a case where the waistband 80 is in an inappropriately bent state, the wearing helper is able to suppress the leakage of excrement through the waist opening 66 by correcting the waistband 80 into an appropriate state, and thus it is possible to make the wearing helper feel secure about a concern of leakage.

In addition, in a case where the wearing helper visually recognizes the disposable diaper 10 in the natural state of half fold from the waist opening side (for example, a case where a plurality of the disposable diapers 10 is accommodated in a package piece), since a part of the waistband 80 is exposed on the outer side of the rear end edge 11R of the body portion 11 in the front-rear direction L, the waistband 80 is positioned near the point of view of the wearing helper compared with a case where the waistband 80 is not exposed. Therefore, in a top view of the disposable diaper 10 (that is, when viewed from the waist opening side), it becomes easy for the wearing helper to visually recognize the waistband 80.

As shown in FIG. 6B and FIG. 7, according to one or more embodiments, in the natural state of half fold, a part of the waistband 80 is exposed on the outer side of the front end edge 11F of the body portion 11 in the front-rear direction L. In the other words, in the natural state of half fold, a part of the waistband 80 protrudes from the front end edge 11F of the body portion 11 in the front-rear direction L. Therefore, the waistband 80 has a second exposed portion 882 (exposed portion 88) that is exposed from the body portion 11 in the natural state of half fold. The second exposed portion 882 is a portion of the waistband 80 that is exposed on the outer side of the front end edge 11F of the body portion 11 in the front-rear direction L in the natural state of half fold. In the natural state of half fold, since parts of the waistband 80 are exposed on the outer sides in the front-rear direction L of not only the rear end edge 11R of the body portion 11 but also the front end edge 11F of the body portion 11, it is possible to visually recognize the parts of the waistband 80 in a plan view of the disposable diaper 10 from the front waistline region S1 side. Therefore, for the wearing helper, even before the use of the disposable diaper, it becomes easier to visually recognize the parts of the waistband 80 that is exposed from the body portion and to recognize the waistband 80.

As shown in FIGS. 8A and 8B, the skin contact portion 851 that is not joined to the body portion 11 has an outer skin contact portion 851O and an inner skin contact portion 851I.

The outer skin contact portion 851O is a portion on the outer side of a center C1 of the skin contact portion 851 in the front-rear direction L. The inner skin contact portion 851I is a portion on the inner side of the center C1. The contractive force of the inner skin contact portion 851I in the width direction W may be greater than the contractive force of the outer skin contact portion 851O in the width direction W. In this case, the inner skin contact portion 851I contracts in the width direction W more than the outer skin contact portion 851O. Therefore, the length of the inner skin contact portion 851I in the width direction W becomes shorter than the length of the outer skin contact portion 851O in the width direction. Since the outer skin contact portion 851O and the inner skin contact portion 851I are configuring the same skin contact portion 851, a portion of the outer skin contact portion 851O close to the inner skin contact portion 851I further contracts due to the contraction of the inner skin contact portion 851I. On the other hand, a portion of the outer skin contact portion 851O far from the inner skin contact portion 851I is unlikely to be affected by the contraction of the inner skin contact portion 851I and is unlikely to contract due to the contraction of the inner skin contact portion 851I. Therefore, as shown in FIG. 8B, the skin contact portion 851 is likely to deform in an arc shape such that the center of the skin contact portion 851 in the width direction W protrudes toward the outer side (rear side) in the front-rear direction L. With this configuration, the center of the skin contact portion 851 in the width direction is likely to protrude toward the outer side in the front-rear direction L more than the end portions of the skin contact portion 851 in the width direction W. As shown in FIG. 6A, even in a case where the end portions of the skin contact portion 851 in the width direction W are not exposed from the body portion 11, the center of the skin contact portion 851 in the width direction W is exposed from the body portion 11, and it becomes easy for the wearing helper to recognize the waistband 80. It should be noted that the skin contact portion 851 is wrinkled due to contraction and thus may not deform in a clear arc shape as shown in FIG. 8B. The center of the skin contact portion 851 in the width direction W may protrude to the rear side more than the end portions of the skin contact portion 851 in the width direction W.

The "contractive force" may be measured by the following method. When the contractive force is measured, a test piece that serves as a measurement object is produced. Both end portions of the test piece are clamped with chucks (clamping tools) of a tensile tester. At this time, the distance between the chucks is set to 50 mm. Next, in a state in which one of the chucks in the width direction W is fixed, the other chuck is moved such that the distance between the chucks changes. The movement speed of the chuck at this time is set to 300 mm/min. During the movement of the chuck, a stress that is applied to the chuck is measured, and a stress (N) obtained in a state in which the width of the test piece reaches 60% (constant width) of the width in the stretched state is defined as the "contractive force".

As shown in FIGS. 9A and 9B, the body portion 11 has the waist contraction region WR that is formed of the waist-around elastic member 45. The waist contraction region WR extends in the width direction W so as to straddle the center of the body portion 11 in the width direction W. The waist contraction region WR contracts in the width direction W. Due to the contraction of the waist contraction region WR, the body portion 11 having the waist contraction region WR also contracts. An overlapped portion WR1 in the inner side portion of the waist contraction region WR in the front-rear direction L that overlaps the absorbent core 31 is unlikely to contract in the width direction W due to the stiffness of the absorbent core 31 compared with an outer side portion WR2 of the waist contraction region WR in the front-rear direction L. Therefore, the length in the width direction W of the body portion that overlaps the overlapped portion WR1 of the waist contraction region WR in the thickness direction T becomes longer than the length in the width direction W of the body portion 11 that overlaps the outer side portion WR2 of the waist contraction region WR in the thickness direction T. Therefore, as shown in FIG. 9B, (the rear end edge 11R of) the body portion 11 is more likely to deform in an arc shape in an extension region ER that is a region extended from the absorbent core 31 such that the center of the rear end edge 11R of the body portion 11 in the width direction W is recessed toward the inner side. Therefore, even in a case where the end portions of the waistband 80 in the width direction W are not exposed from the body portion 11, the center of the waistband 80 in the width direction W is further exposed from the body portion 11, and it becomes easy for the wearing helper to recognize the waistband. It should be noted that (the rear end edge 11R of) the body portion 11 is wrinkled due to contraction and thus may not deform in a clear arc shape as shown in FIG. 9B. The center (of the rear end edge 11R) of the body portion 11 in the width direction W may be recessed toward the crotch region S3.

In addition, as shown in FIG. 1 and FIG. 2, the waistband 80 may have the pair of side joining portions (second joining portions) 842. Each of the pair of side joining portions 842 may be positioned on the outer side of the outer side edge 31E of the absorbent core 31 in the width direction W. In other words, each of the pair of side joining portions 842 may be disposed more on an outer side in the width direction W than the outer side edge 31E of the absorbent core 31. Therefore, at least a part of each of the pair of side joining portions 842 is positioned away from the absorbent core 31 and the extension region ER. Therefore, as shown in FIG. 9B, even when the body portion 11 deforms in an arc shape in the extension region ER such that the center of the rear end edge 11R of the body portion 11 in the width direction W is recessed toward the inner side, the side joining portions 842 that are positioned away from the extension region ER are not affected by the deformation of the body portion 11. With this configuration, it is possible to suppress the center of the waistband 80 in the width direction being recessed toward the inner side (the crotch region S3 side) and to suppress a decrease in the amount of the waistband 80 exposed from the body portion 11. When a decrease in the amount of the waistband 80 exposed is suppressed, even before the use of the disposable diaper, it becomes easy for the wearing helper to visually recognize a part of the waistband 80 and to recognize the waistband 80. As in one or more embodiments, the inner side edges of the pair of side joining portions 842 may be positioned on the outer sides of the outer side edges 31E of the absorbent core 31 in the width direction W. Therefore, the pair of side joining portions 842 is positioned away from the absorbent core 31 and the extension region ER and is thus not affected by the deformation of the body portion 11.

It should be noted that, as the distance between the inner side edges of the pair of side joining portions 842 increases, it becomes easier for the center of the non-joining portion 85 (rising portion 852) in the width direction W to move in the front-rear direction L since the center of the non-joining portion 85 (rising portion 852) becomes farther from the side joining portions 842. Therefore, due to the contraction of the waistband 80 described above, the distance that the center of the non-joining portion 85 (rising portion 852) in the width direction W protrudes (extends) toward the outer side in the front-rear direction L increases. Therefore, the positions of the inner side edges of the pair of side joining portions 842 on the outer sides of the outer side edges 31E of the absorbent core 31 in the width direction W increases the distance that the non-joining portion 85 protrudes (extends) toward the outer side in the front-rear direction L, and thus it is possible to increase the amount of the waistband 80 exposed.

As shown in FIG. 1, each of the pair of side joining portions 842 may be positioned on the outer side of the leak-proof elastic member 61 in the width direction W. In other words, each of the pair of side joining portions 842 may be disposed more on an outer side in the width direction W than the leak-proof elastic member 61. The pair of side joining portions 842 is unlikely to be directly affected by the contraction of the leak-proof elastic members 61. Therefore, it becomes difficult for the waistband 80 to be pulled toward the inner side (toward crotch region S3) in the front-rear direction L, and it is possible to suppress a decrease in the amount of the waistband 80 exposed from the body portion 11. When a decrease in the amount of the waistband 80 exposed is suppressed, even before the use of the disposable diaper 10, it becomes easy for the wearing helper to visually recognize a part of the waistband 80 and to recognize the waistband 80.

As in one or more embodiments, the inner side edges of the pair of side joining portions 842 may be positioned on the outer sides of the leak-proof elastic members 61 in the width direction W. With this configuration, the pair of side joining portions 842 are unlikely to be directly affected by the contraction of the leak-proof elastic members 61, and it is possible to suppress a decrease in the amount of the waistband 80 exposed from the body portion 11. Additionally, since the positions of the inner side edges of the pair of side joining portions 842 on the outer sides of the leak-proof elastic members 61 in the width direction W further increases the distance that the non-joining portion 85 protrudes (extends) toward the outer side in the front-rear direction L, and thus it is possible to further increase the amount of the waistband 80 exposed.

As shown in FIG. 1, each of the pair of side joining portions 842 may be positioned on the outer side of the first leak-proof base end edge 641 in the width direction W. In other words, each of the pair of side joining portions 842 may be disposed more on an outer side in the width direction W than the first leak-proof base end edge 641. Therefore, the pair of side joining portions 842 is unlikely to be affected by the contraction of the contraction portions 63. Therefore, it becomes difficult for the waistband 80 to be pulled toward the inner side (toward crotch region S3) in the front-rear direction, and it is possible to suppress a decrease in the amount of the waistband 80 exposed from the body portion 11. Even before the use of the disposable diaper 10, it becomes easy for the wearing helper to notice a part of the waistband 80 and to visually recognize the waistband 80.

As in one or more embodiments, the inner side edges of the pair of side joining portions 842 may be positioned on the outer sides of the first leak-proof base end edges 641 in the width direction W. With this configuration, the pair of side joining portions 842 is unlikely to be affected by the contraction of the contraction portion 63, and it is possible to suppress a decrease in the amount of the waistband 80 exposed from the body portion 11. Additionally, since the positions of the inner side edges of the pair of side joining portions 842 on the outer sides of the first leak-proof base end edges 641 in the width direction W further increases the distance that the non-joining portion 85 protrudes (extends) toward the outer side in the front-rear direction L, and thus it is possible to further increase the amount of the waistband 80 exposed.

As shown in FIG. 1, the pair of side joining portions 842 may be positioned on the outer side of the second leak-proof base end edges 642 that are arranged on the rear waistline region S2 side in the front-rear direction L. With this configuration, the pair of side joining portions 842 is unlikely to be affected by the contraction of the contraction portions 63. Therefore, it becomes difficult for the waistband 80 to be pulled toward the inner side (toward crotch region S3) in the front-rear direction, and it is possible to suppress a decrease in the amount of the waistband 80 exposed from the body portion 11.

In addition, as the distance between the inner side edges of the pair of skin contact joining portions 853 increases, it becomes easier for the center of the non-joining portion 85 (skin contact portion 851) in the width direction W to move in the front-rear direction L since the center of the non-joining portion 85 (skin contact portion 851) becomes farther from the side joining members 833. That is, the distance that the center of the non-joining portion 85 (skin contact portion 851) in the width direction W protrudes (extends) toward the outer side in the front-rear direction L increases. Therefore, the positions of the inner side edges of the pair of skin contact joining portions 853 on the outer sides of the outer side edges 31E of the absorbent core 31 in the width direction W increases the distance that the non-joining portion 85 protrudes (extends) toward the outer side in the front-rear direction L, and thus it is possible to increase the amount of the waistband 80 exposed.

In addition, since the positions of the inner side edges of the pair of skin contact joining portions 853 on the outer sides of the leak-proof elastic members 61 in the width direction W further increases the distance that the non-joining portion 85 protrudes toward the outer side in the front-rear direction L, it is possible to further increase the amount of the waistband 80 exposed. In addition, since the positions of the inner side edges of the pair of skin contact joining portions 853 on the outer sides of the first leak-proof base end edges 641 in the width direction W further increases the distance that the non-joining portion 85 protrudes toward the outer side in the front-rear direction L, it is possible to further increase the amount of the waistband 80 exposed.

(5) Modification Example

Figure 10:
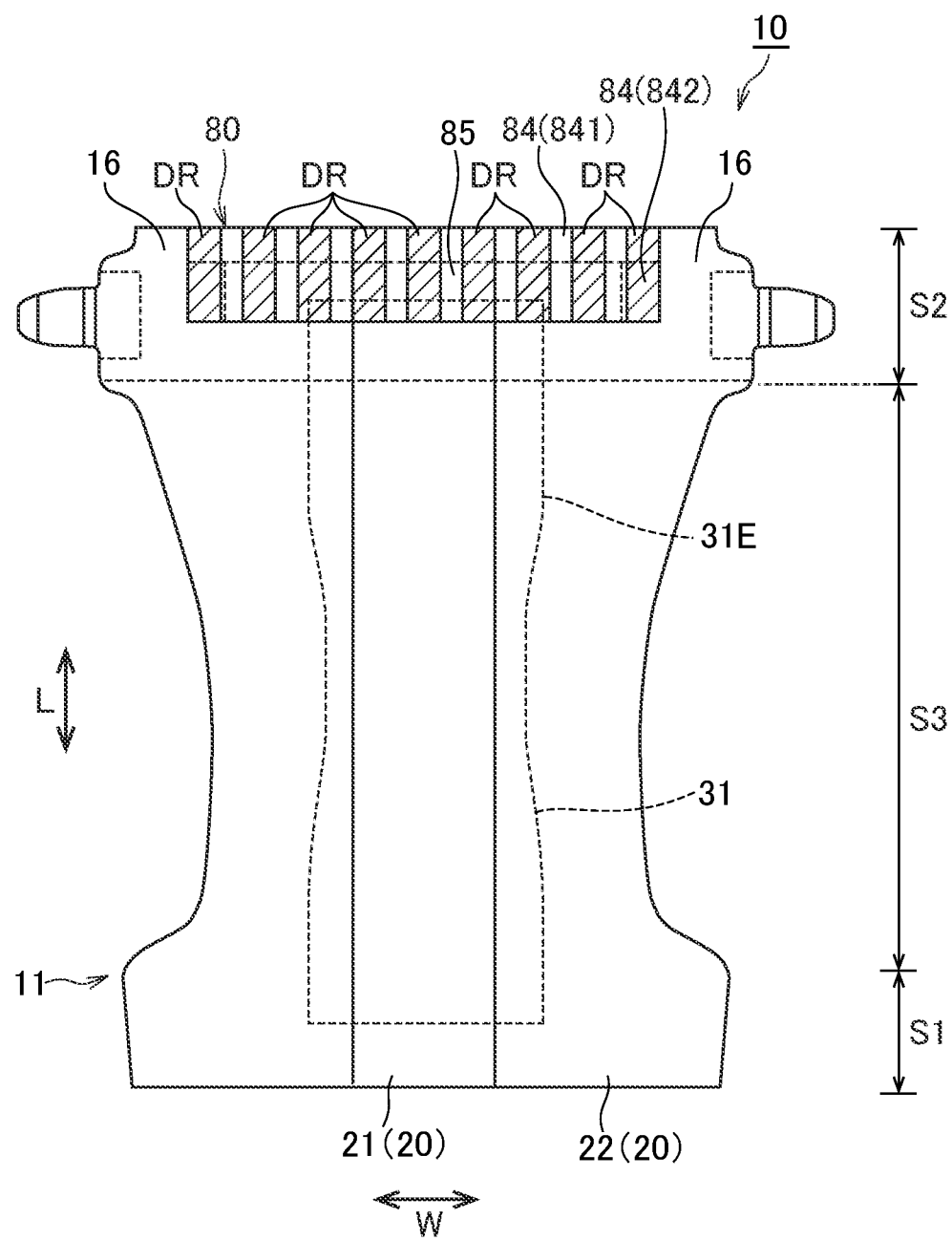
FIG. 10 is a schematic plan view of a disposable diaper according to a modification example as viewed from the skin facing surface side.
Figure 11A:
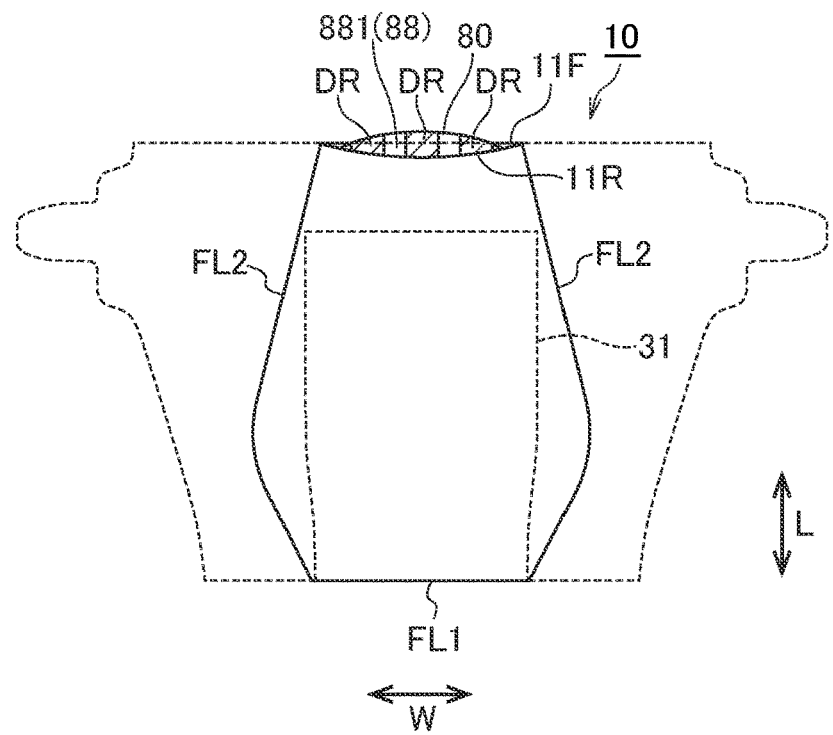
FIGS. 11A and 11B are schematic plan views of the disposable diaper according to the modification example in a natural state of half fold.
Figure 11B:
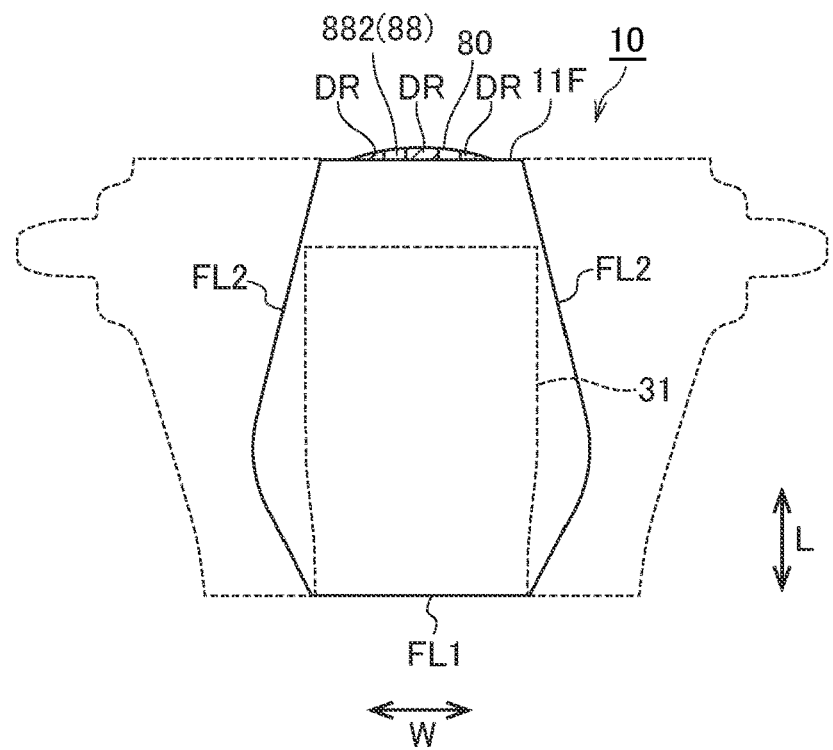

Next, a modification example will be described using FIG. 10 and FIG. 11. FIG. 10 is a schematic plan view of a disposable diaper 10 according to the modification example as viewed from the skin facing surface side T1. FIG. 11 is a schematic plan view of the disposable diaper 10 according to the modification example in a natural state of half fold. FIG. 11A is a schematic plan view of the disposable diaper 10 in a natural state of half fold as viewed from the rear waistline region S2 side. FIG. 11B is a schematic plan view of the disposable diaper 10 in the natural state of half fold as viewed from the front waistline region S1 side. It should be noted that the same portion as in the above-described embodiment will not be described.

As shown in FIG. 10, the waistband 80 may be provided with a design that is visually recognizable from the skin facing surface side T1 of the disposable diaper 10. The waistband 80 may have design regions DR in which the design is provided. When the wearing helper puts the disposable diaper 10 on the wearer, the eyes are caught on the designs, and it becomes easy to recognize the waistband 80 provided with the designs. Once the wearing helper recognizes the waistband 80, it is possible to reduce a concern of the leakage of excrement through the waist opening 66 and to make the wearing helper feel secure about a concern of leakage. In addition, in a case where the wearing helper recognizes the waistband 80, it becomes easy to find out that the waistband 80 is in an inappropriately bent state. In a case where the waistband 80 is in an inappropriately bent state, the wearing helper corrects the waistband 80 into an appropriate state, whereby the accommodation space AS that opens toward the crotch region S3 appropriately functions as a pocket that accommodates excrement that moves toward the waist opening 66. Therefore, it is possible to suppress the leakage of excrement through the waist opening 66, and thus it is possible to make the wearing helper feel secure about a concern of leakage.

As shown in FIGS. 11A and 11B, the exposed portion 88 may be provided with a design that is visually recognizable in the natural state of half fold. With this configuration, when the wearing helper puts the disposable diaper 10 on the wearer, the eyes are caught on the design, and it becomes easy to recognize the waistband provided with the design.

As shown in FIG. 11A, in the natural state of half fold, the design regions DR may be exposed on the outer side (rear side) of the rear end edge 11R of the body portion 11 in the front-rear direction L. That is, the first exposed portion 881 may be provided with a design. With this configuration, in the natural state of half fold, the designs provided in the waistband 80 may be visually recognizable from the non-skin facing surface side T2 on the back side of the wearer. When the wearing helper puts the disposable diaper on the wearer, the eyes are caught on the designs, and it becomes easy to recognize the waistband provided with the designs. In order to make it easy for the designs provided in the waistband 80 to be visually recognized from the non-skin facing surface side T2 on the back side of the wearer, the design regions DR may be provided on the non-skin facing surface side T2 of the first exposed portion 881 (specifically, on the skin facing surface side T1 or the non-skin facing surface side T2 of the second nonwoven fabric layer 812 or on the non-skin facing surface side T2 of the film layer 813).

As shown in FIG. 11B, in the natural state of half fold, the design regions DR may be exposed on the outer side (front side) of the front end edge 11F of the body portion 11 in the front-rear direction L. That is, the second exposed portion 882 may be provided with a design. With this configuration, in the natural state of half fold, the designs provided in the waistband 80 may be visually recognizable from the skin facing surface side T1 on the ventral side of the wearer. When the wearing helper puts the disposable diaper on the wearer, the eyes are caught on the designs, and it becomes easy to recognize the waistband provided with the designs. In order to make it easy for the designs provided in the waistband 80 to be visually recognized from the skin facing surface side T1 on the ventral side of the wearer, the design regions DR may be provided on the skin facing surface side T1 of the second exposed portion 882 (specifically, on the skin facing surface side T1 or the non-skin facing surface side T2 of the first nonwoven fabric layer 811 or on the skin facing surface side T1 of the film layer 813).

It should be noted that, in a stretched state of the disposable diaper 10, the rear end edges of the design regions DR may be arranged on the rear side of rear end edges 93R of the locking portions 93 and may be arranged on the rear side of rear end edges 90R of the fastening tapes 90. With this configuration, since the design regions DR are arranged on the waist opening 66 side, it becomes easy for the designs to be exposed from at least one of the front end edge 11F and the rear end edge 11R of the body portion 11. Therefore, it is possible to enhance the visibility of the waistband 80.

It should be noted that the expression "visually recognizable" means that a human subject who has good visual acuity (1.0 or more) in both eyes is able to visually recognize an object when seeing the object at a distance of approximately 30 to 50 cm in a room brightly illuminated (reference: 500 to 750 lx (Lux)) with neutral white (color temperature reference of 4,600 to 5,400 K (Kelvin)).

The design is formed of a pattern (a combination of a shape and a color). For example, as shown in FIG. 11, the design may be formed of a vertical stripe extending in the front-rear direction L. With this configuration, in a case where the waistband 80 is configured to be stretchable in the width direction W, the stretching of the waistband 80 in the width direction W also stretches the vertical stripe and changes the length of the vertical stripe in the width direction. With this configuration, since the wearing helper is able to feel the fitting property of the waistband with respect to the body, it is possible to reduce a concern of the leakage of excrement through the waist opening 66 and to make the wearing helper feel secure about a concern of leakage. The design may be formed of at least any of a horizontal stripe extending in the width direction W, a round shape, a star shape, a heart shape, and the like.

In the design, a color darker than the colors of the members that configure the body portion 11 may be used or a larger number of colors than the number of the colors of the members that configure the body portion 11 (the skin surface side sheet 20, the non-skin surface side sheet 25, and the like) may be used. With this configuration, the waistband 80 becomes more noticeable, the eyes of the wearing helper are caught on the design, and it becomes easy to recognize the waistband provided with the design. In addition, the fact that the color of the design is a dark color and/or the design has a plurality of colors makes it difficult for excrement accommodated in the accommodation space AS to be noticeable. It becomes easy to make the wearing helper feel secure about a concern of leakage. In addition, even when excrement accommodated in the accommodation space AS oozes, the excrement that has oozed overlaps the design or is adjacent to the design, which makes it difficult for the excrement to become noticeable. Therefore, it becomes difficult for the wearing helper to sense the oozing of excrement after use, and it becomes easier to make the wearing helper feel secure about a concern of leakage.

The design may be provided by being printed on a member that configures the waistband 80 (nonwoven fabric, a film, or the like). In addition, the design may be provided with a colored member that configures the waistband 80 (nonwoven fabric, a film, or the like). A colored portion may configure the design. In addition, the design may be provided by, for example, joining a heat seal having designability such as a heart shape or a star shape to the waistband 80. The design may be provided by shaping the waistband 80. A pattern or a shape formed of, for example, a wavy line or a dot line may be drawn on the waistband 80 by shaping.

The design (design region DR) may be provided in the band stretch/contraction region BSR. When the wearing helper puts the disposable diaper 10 on the wearer, the disposable diaper 10 is stretched by pulling both sides of the disposable diaper 10 in the width direction W, whereby the band stretch/contraction region BSR stretches in the width direction W, and the design provided in the band stretch/contraction region BSR also stretches. With this configuration, since the wearing helper is able to feel the fitting property of the waistband 80 with respect to the body, it is possible to reduce a concern of the leakage of excrement through the waist opening 66 and to make the wearing helper feel secure about a concern of leakage.

(6) Other Embodiments

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

In the above-described embodiment, the waistband 80 is arranged in the rear waistline region S2, but the configuration is not limited thereto. The waistband 80 may be arranged in the front waistline region S1 or may be arranged in both the front waistline region S1 and the rear waistline region S2. In the above-described disposable diaper 10, the first nonwoven fabric layer 811 and the second nonwoven fabric layer 812 are made of the same nonwoven fabric, but may be made of different nonwoven fabrics.

In the above description, the band elastic members 82 may not be arranged in the waistband 80, and the band elastic members 82 may be arranged in one of the skin contact portion 851 and the rising portion 852 or may be arranged in both the skin contact portion 851 and the rising portion 852. In a case where the band elastic members 82 are arranged in the skin contact portion 851, since the waistband 80 fits the body, it is possible to suppress the leakage of excrement through the waist opening 66. In addition, in a case where the band elastic members 82 are arranged in the rising portion 852, since the rising property of the waistband 80 is enhanced, the waistband 80 comes close to the body, and it is possible to suppress the leakage of excrement through the waist opening 66.

In addition, in a stretched state of the disposable diaper 10, the rear end edge of the design region DR may be away toward the front side from the rear end edge 80R of the waistband 80. In addition, in a stretched state of the disposable diaper 10, the rear end edge of the design region DR may be positioned on the front side of the rear end edge 11R of the body portion 11. Here, in a case where the disposable diaper 10 is produced by cutting a continuous sheet after the waistband 80 is arranged on the continuous sheet, there is a case where the design region DR is also cut due to the fact that the waistband 80 is cut together with the continuous sheet. In this case, the waistband 80 is provided with an incomplete design. The rear end edge of the design region DR may be away toward the front side from the rear end edge 11R of the waistband 80 in order not to provide an incomplete design to the waistband 80.

In addition, the first nonwoven fabric layer 811 provided with the design or the film layer 813 provided with the design may be arranged on the skin facing surface side T1 of the band elastic members 82 such that the design region DR is provided on the skin facing surface side T1 of the band elastic members 82 in the skin contact portion 851.

In the above-described embodiment, the waist contraction region WR formed of the waist-around elastic member 45 overlaps the absorbent core 31 in the thickness direction T, but the configuration is not limited thereto. The waist-around elastic member 45 may not overlap the absorbent core 31 in the thickness direction T. Specifically, the waist-around elastic member 45 may be arranged on the outer side of the absorbent core 31 in the width direction W. In this case, the inner side portion of the waist contraction region WR in the front-rear direction L is arranged on the absorbent core 31 side compared with the outer side portion of the waist contraction region WR in the front-rear direction. Therefore, in the region on the absorbent core 31 and the region extended from the absorbent core 31 in the front-rear direction L, the inner side portion of the waist contraction region WR is unlikely to contract in the width direction W compared with the outer side portion of the waist contraction region WR due to the stiffness of the absorbent core 31. With this configuration, the length in the width direction W of the body portion 11 that overlaps the outer side portion of the waist contraction region WR in the thickness direction T is likely to become shorter than the length of the body portion 11 that overlaps the inner side portion of the waist contraction region WR in the thickness direction T, and the body portion 11 deforms in an arc shape in the region extended from the absorbent core 31 such that the center of the rear end edge 11R of the body portion 11 in the width direction W is recessed toward the inner side. Therefore, even in a case where the end portions of the waistband 80 in the width direction W are not exposed from the body portion 11, the center of the waistband 80 in the width direction W is exposed from the body portion 11, and it becomes easy for the wearing helper to recognize the waistband.

It should be noted that the waist-around elastic member 45 may be arranged in the waistline region (the front waistline region S1 and/or the rear waistline region S2) in which the waistband 80 is arranged. In the above-described embodiment, the disposable diaper 10 is a tape-type disposable diaper, but the configuration is not limited thereto. The disposable diaper 10 may be a pants-type disposable diaper. The configurations of the disposable diapers 10 according to the above-described embodiment, modification example, and other configurations can be appropriately combined together.

According to one or more embodiments, it is possible to provide a disposable diaper including a waistband which reduces a concern of the leakage of excrement through the waist opening and easily makes wearing helpers feel secure.

10: Disposable diaper, 11: body portion, 16: side flap, 20: skin surface side sheet, 21: top-surface sheet, 22: side sheet, 23: back-surface sheet, 24: exterior sheet, 25: non-skin surface side sheet, 31: absorbent core, 42: leg-around elastic member, 45: waist-around elastic member, 60: leak-proof gather, 61: leak-proof elastic member, 63: contraction portion, 64: leak-proof base end edge, 65: Leg opening, 66: waist opening, 80: waistband, 81: sheet layer, 82: band elastic member, 83: joining member, 84: joining portion, 85: non-joining portion, 88: exposed portion, 90: fastening tape, 92: base portion, 93: locking portion, 95: target portion, 641: first leak-proof base end edge, 642: second leak-proof base end edge, 811: first nonwoven fabric layer, 812: second nonwoven fabric layer, 813: film layer, 831: first joining member, 832: second joining member, 833: side joining member, 841: first joining portion, 842: second joining portion (side joining portion), 851: skin contact portion, 851I: inner skin contact portion, 851O: outer skin contact portion, 851S: skin contact surface, 852: rising portion, 853: skin contact joining portion, 881: first exposed portion, 882: second exposed portion, AS: accommodation space, BSR: band stretch/contraction region, ER: extension region, S1: front waistline region, S2: rear waistline region, S3: crotch region, WR: waist contraction region

What is claimed is:

1. A disposable diaper having a front-rear direction and a width direction that is orthogonal to the front-rear direction, the disposable diaper comprising:
   a first waistline region;
   a second waistline region;
   a crotch region disposed between the first waistline region and the second waistline region;
   an absorbent core;
   a waistband disposed in the first waistline region;
   a body portion that comprises the absorbent core and is disposed on a non-skin facing surface side of the waistband;
   a space that opens toward the crotch region disposed on the non-skin facing surface side of the waistband; and
   a fold line in the crotch region extending in the width direction, wherein
   the body portion comprises a first outer end edge that is an outer end edge in the front-rear direction in the first waistline region,
   in a pre-wearing state in which the waistband is sandwiched by the body portion and the disposable diaper is folded at the fold line as a base point, a part of the waistband protrudes from the first outer end edge in the front-rear direction,
   the body portion comprises a second outer end edge that is an outer end edge in the front-rear direction in the second waistline region,
   in the pre-wearing state, the part of the waistband protrudes from the second outer end edge in the front-rear direction,
   the fold line is disposed in a vicinity of a center of the disposable diaper in the front-rear direction, and
   the waistband comprises a non-joining portion that is not joined to the body portion, wherein the non-joining portion:
      is folded back to an outer side in the front-rear direction at a band fold line extending in the width direction as a base point, and
      comprises a folded-back portion that extends from the band fold line toward the outer side in the front-rear direction.

2. The disposable diaper according to claim 1, wherein
   the waistband comprises a skin contact portion that comprises a skin contact surface that comes into contact with a skin of a wearer,
   the skin contact portion that is not joined to the body portion comprises:
      an outer skin contact portion that is an outer side portion relative to a center of the skin contact portion in the front-rear direction; and
      an inner skin contact portion that is an inner side portion relative to the center of the skin contact portion in the front-rear direction, and
   a contractive force of the inner skin contact portion in the width direction is greater than a contractive force of the outer skin contact portion in the width direction.

3. The disposable diaper according to claim 1, wherein
   the body portion comprises a waist contraction region that is disposed at least in the first waistline region,
   the waist contraction region extends in the width direction and straddle a center of the body portion in the width direction, and
   the waist contraction region contracts in the width direction.

4. The disposable diaper according to claim 3, wherein an inner end edge of the waist contraction region in the front-rear direction overlaps the absorbent core in a thickness direction.

5. The disposable diaper according to claim 3, wherein
   the waistband comprises a pair of side joining portions that is disposed at both end portions of the waistband in the width direction and is joined to the body portion, and
   each of the pair of side joining portions is disposed more on an outer side in the width direction than an outer side edge of the absorbent core.

6. The disposable diaper according to claim 1, wherein
   the body portion comprises a skin surface side sheet that is disposed on a skin facing surface side of the absorbent core,
   the skin surface side sheet comprises a top-surface sheet and a pair of side sheets that covers both outer side portions of the top-surface sheet,
   each of the pair of side sheets is a leak-proof gather comprising a contraction portion that rises due to contraction of a leak-proof elastic member that extends in the front-rear direction,
   the waistband comprises a pair of side joining portions that is disposed at both end portions of the waistband in the width direction and is joined to the body portion, and
   each of the pair of side joining portions is disposed more on an outer side in the width direction than the leak-proof elastic member.

7. The disposable diaper according to claim 6, wherein
   the leak-proof gather comprises a base end edge that acts as a rising fulcrum of the contraction portion,
   the base end edge is disposed more on an outer side in the width direction than the contraction portion, and
   each of the pair of side joining portions is disposed more on an outer side in the width direction than the base end edge.

8. The disposable diaper according to claim 1, wherein
   the waistband further comprises joining portion joined to the body portion,
   the non-joining portion further comprises a rising portion that extends inward in the front-rear direction from the joining portion to the band fold line and is capable of rising,
   the folded-back portion is positioned on a skin facing surface side of the rising portion, and
   a total length of a length from one end edge to another end edge of the rising portion in the front-rear direction and a length from one end edge to the another end edge of the folded-back portion in the front-rear direction is longer than a length from a boundary between the joining portion and the rising portion to the first outer end edge.

9. The disposable diaper according to claim 8, wherein the length from the one end edge to the another end edge of the rising portion in the front-rear direction is longer than the length from the boundary between the joining portion and the rising portion to the first outer end edge.

10. The disposable diaper according to claim 1, wherein the fold line is visible when the disposable diaper is unfolded.

11. A disposable diaper having a front-rear direction and a width direction that is orthogonal to the front-rear direction, the disposable diaper comprising:
   a first waistline region;
   a second waistline region;

a crotch region disposed between the first waistline region and the second waistline region;

an absorbent core;

a waistband disposed in the first waistline region;

a body portion that comprises the absorbent core and is disposed on a non-skin facing surface side of the waistband; and a space that opens toward the crotch region disposed on the non-skin facing surface side of the waistband, wherein the body portion comprises a first outer end edge that is an outer end edge in the front-rear direction in the first waistline region, in a pre-wearing state in which the waistband is sandwiched by the body portion and the disposable diaper is folded at a fold line extending in the width direction as a base point in the crotch region, a part of the waistband protrudes from the first outer end edge in the front-rear direction, the fold line is disposed in a vicinity of a center of the disposable diaper in the front-rear direction, and the waistband comprises a non-joining portion that is not joined to the body portion, wherein the non-joining portion:

is folded back to an outer side in the front-rear direction at a band fold line extending in the width direction as a base point, and comprises a folded-back portion that extends from the band fold line toward the outer side in the front-rear direction.

* * * * *